US012579795B2

(12) United States Patent
Kubota et al.

(10) Patent No.: US 12,579,795 B2
(45) Date of Patent: Mar. 17, 2026

(54) DIAGNOSIS SUPPORT SYSTEM, DIAGNOSIS SUPPORT METHOD, AND STORAGE MEDIUM

(71) Applicant: OLYMPUS CORPORATION, Tokyo (JP)

(72) Inventors: Akihiro Kubota, Kokubunji (JP); Yamato Kanda, Hino (JP); Katsuyoshi Taniguchi, Hino (JP); Naohisa Takabatake, Kawasaki (JP); Takashi Kono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 625 days.

(21) Appl. No.: 18/076,663

(22) Filed: Dec. 7, 2022

(65) Prior Publication Data

US 2023/0100147 A1 Mar. 30, 2023

Related U.S. Application Data

(63) Continuation of application No. PCT/JP2020/029636, filed on Aug. 3, 2020.

(51) Int. Cl.
G06K 9/00 (2022.01)
G06T 7/00 (2017.01)
(Continued)

(52) U.S. Cl.
CPC .......... G06V 10/776 (2022.01); G06T 7/0012 (2013.01); G06V 10/25 (2022.01);
(Continued)

(58) Field of Classification Search
CPC ............ G06N 20/00; G06N 3/08; G06N 7/01; G06N 3/045; G06N 5/04; G06N 20/20;
(Continued)

(56) References Cited

U.S. PATENT DOCUMENTS 10,456,009 B2 10/2019 Kamiyama et al.
11,457,799 B2 10/2022 Nadimi et al.
(Continued)

FOREIGN PATENT DOCUMENTS

JP 2002-165757 A 6/2002
WO 2016/185617 A1 11/2016
(Continued)

OTHER PUBLICATIONS

International Search Report dated Sep. 15, 2020 received in PCT/JP2020/029636.
(Continued)

*Primary Examiner* — Alex Kok S Liew
(74) *Attorney, Agent, or Firm* — Scully, Scott, Murphy & Presser, P.C.

(57) ABSTRACT

A diagnosis support system includes a processor. The processor is connected to a plurality of classifiers that are different in performance. The processor displays performance information of each of the classifiers side by side, receives a user's selection of the performance information displayed side by side, and inputs an input image to the classifier associated with the performance information selected by the user.

25 Claims, 13 Drawing Sheets

(51) Int. Cl.
| | |
|---|---|
| *G06V 10/25* | (2022.01) |
| *G06V 10/764* | (2022.01) |
| *G06V 10/776* | (2022.01) |
| *G06V 10/94* | (2022.01) |
| *A61B 1/00* | (2006.01) |

(52) U.S. Cl.
CPC .......... *G06V 10/764* (2022.01); *G06V 10/945* (2022.01); *A61B 1/000096* (2022.02); *G06T 2207/10068* (2013.01); *G06T 2207/20092* (2013.01); *G06T 2207/30096* (2013.01); *G06V 2201/03* (2022.01)

(58) Field of Classification Search
CPC ............ G06N 3/04; G06N 5/01; G06N 5/022; G06N 3/008; G06N 3/044; G06N 3/0464; G06N 3/082; G06N 3/084; G06F 16/35; G06F 40/30; G06F 16/3329; G06F 16/353; G06F 16/93; G06F 18/211; G06F 18/254; G06F 40/279; G06F 40/284; G06F 16/3331; G06F 16/338; G06F 16/906; G06F 18/2415; G06F 21/32; G06T 2207/20081; G06T 7/0012; G06T 2207/30096; G06T 7/11; G06T 2207/10081; G06T 2207/10132; G06T 2207/30061; G06T 2207/20076; G06T 2207/30101; G06T 7/0004; G06T 7/0014; G06T 7/68; G06T 2207/20084; G06T 2207/20104; G06T 7/0016; G06T 2207/10024; G06T 2207/10072; G06T 2207/10116
See application file for complete search history.

(56) References Cited

U.S. PATENT DOCUMENTS

| | | | |
|---|---|---|---|
| 11,483,473 B2 | 10/2022 | Shiraki et al. | |
| 2004/0218806 A1* | 11/2004 | Miyamoto | ............. G06F 18/40 |
| | | | 382/145 |
| 2009/0214099 A1* | 8/2009 | Merlet | ...................... G06T 7/11 |
| | | | 382/275 |

| | | | |
|---|---|---|---|
| 2014/0200433 A1* | 7/2014 | Choi | ................... G06V 10/809 |
| | | | 600/407 |
| 2017/0039345 A1* | 2/2017 | Röder | ................... G16B 40/20 |
| 2017/0146388 A1* | 5/2017 | Kovacs | ................. G01G 19/50 |
| 2017/0357844 A1* | 12/2017 | Comaniciu | ........... G16H 30/00 |

FOREIGN PATENT DOCUMENTS

| | | |
|---|---|---|
| WO | 2018/180573 A1 | 10/2018 |
| WO | 2019/087791 A1 | 5/2019 |
| WO | 2019/122338 A1 | 6/2019 |

OTHER PUBLICATIONS

Liu Ming et al., "Colonic Polyp Detection in Endoscopic Videos with Single Shot Detection Based Deep Convolutional Neural Network", IEEE Access, Jun. 20, 2019, vol. 7, pp. 75058-75066, in particular, IV. Results and Discussion, Tables 2-6, Figures 6-7.

Sekuboyina Anjany Kumar et al., "A Convolutional Neural Network Approach for Abnormality Detection in Wireless Capsule Endoscopy", 2017 IEEE 14th International Symposium on Biomedical Imaging (ISBI 2017), Apr. 21, 2017, pp. 1057-1060, in particular, table 3.

Sakai Y., "Automatic detection of early gastric cancer in endoscopic images using a transferring convolutional neural network", 2018 40th Annual International Conference of the IEEE Engineering in Medicine and Biology Society (EMBC), Jul. 21, 2018, pp. 4138-4141,Figures 4-5.

Hirasawa Toshiaki et al., "Application of artificial intelligence using a convolutional neural network for detecting gastric cancer in endoscopic images", Gastric Cancer, Jan. 15, 2018, vol. 21, pp. 653-660, in particular, table 1.

Aoki Tomonori et al., "Automatic detection of erosions and ulcerations in wireless capsule endoscopy images based on a deep convolutional neural network", Gastrointestinal Endoscopy, Feb. 28, 2019, vol. 89 No. 2, pp. 357-363.e2, in particular, supplementary table 1.

Koide, Tetsushi et al. "Regional Segmentation of Large Intestine NBI Magnifying Endoscopic Images via Pyramid-type Identifiers Using Support Vector Machine"Jun. 13, 2014, IS3-12-1 to IS3-12-7, fig.8, 12, (The 20th Symposium on Sensing via Image Information SSII2014).

* cited by examiner

FIRST CLASSIFIER
CANDIDATE

SECOND CLASSIFIER
CANDIDATE

A1

FIRST CLASSIFIER
CANDIDATE

SECOND CLASSIFIER
CANDIDATE

| | RECALL RATE (%) | | |
|---|---|---|---|
| | PROTRUD-ING LESION | FLAT LESION | DEPRESSED LESION |
| FIRST CLASSIFIER CANDIDATE | 90 | 70 | 50 |
| SECOND CLASSIFIER CANDIDATE | 70 | 85 | 70 |

FIRST CLASSIFIER CANDIDATE　　　SECOND CLASSIFIER CANDIDATE

PROTRUDING LESION　　FLAT LESION　　DEPRESSED LESION　　PROTRUDING LESION　　FLAT LESION　　DEPRESSED LESION

DIAGNOSIS SUPPORT SYSTEM, DIAGNOSIS SUPPORT METHOD, AND STORAGE MEDIUM

CROSS REFERENCE TO RELATED APPLICATION

This application is a continuation of International Patent Application No. PCT/JP2020/029636, having an international filing date of Aug. 3, 2020, which designated the United States, the entirety of which is incorporated herein by reference.

BACKGROUND

In recent years, known is a diagnosis support method (computer aided detection/diagnosis (CAD)) of indicating a position of a lesion candidate and displaying differential information on moving images captured using an endoscope. For example, International Publication No. 2019/087791 discloses a method of performing learning on a new classifier using an image held by a user, and, in a case where the classifier improves in performance in comparison with a reference classifier, changing a classifier. Additionally, International Publication No. 2018/180573 discloses a system of comparing images before and after updating of image processing software.

SUMMARY

In accordance with one of some aspect, there is provided a diagnosis support system comprising a processor, the processor being connected to a plurality of classifiers that are different in performance; the processor displaying performance information of each of the plurality of classifiers side by side; receiving a user's selection of the performance information displayed side by side; and inputting an input image to a corresponding one of the plurality of classifiers, the corresponding one being associated with the performance information selected by the user.

In accordance with one of some aspect, there is provided a diagnosis support method comprising: presenting performance information that is information regarding performance of a plurality of classifiers, the plurality of classifiers outputting mutually different detection results when detecting a region of interest from an input image; receiving a user's selection for selecting at least one of the plurality of classifiers as a classifier serving as an output target; and outputting a detection result of the classifier selected by the user's selection, the presenting including presenting at least two types of performance in a trade-off relationship as the performance information.

In accordance with one of some aspect, there is provided a storage medium storing a diagnosis support program that causes a computer to implement: presenting performance information that is information regarding performance of a plurality of classifiers, the plurality of classifiers outputting mutually different detection results when detecting a region of interest from an input image; receiving a user's selection for selecting at least one of the plurality of classifiers as a classifier serving as an output target; and outputting a detection result of the classifier selected by the user's selection.

DESCRIPTION OF EXEMPLARY EMBODIMENTS

Figure 1:
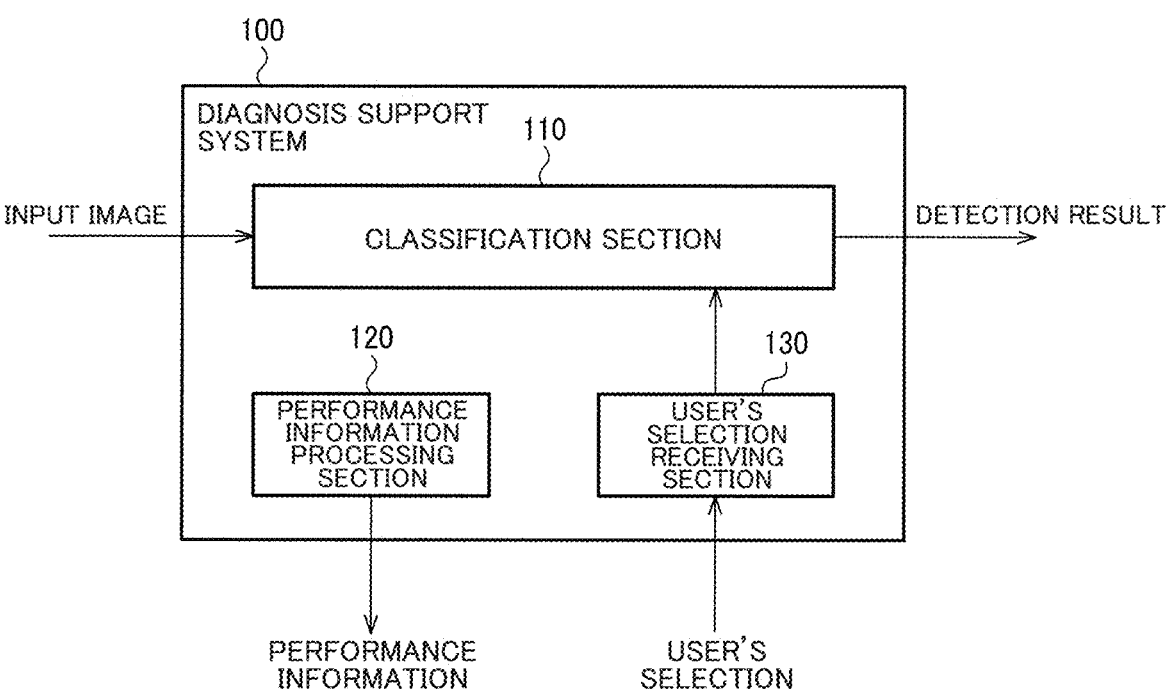
FIG. 1 illustrates a configuration example of a diagnosis support system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Exemplary embodiments are described below. Note that the following exemplary embodiments do not in any way limit the scope of the content defined by the claims laid out herein. Note also that all of the elements described in the present embodiment should not necessarily be taken as essential elements.

1. System Configuration Example

In computer aided detection/diagnosis (CAD), conventionally known are a method of changing a detection sensitivity to a lesion and a method of changing processing depending on an organ. For example, in a case where it is determined that the lesion has been detected on condition that a degree of reliability as an output of a trained model is larger than or equal to a given threshold, it is possible to change a detection sensitivity by changing the threshold. For example, in a case where experienced doctors are targeted, a reduction in detection sensitivity makes a lesion harder to be detected, whereby it is possible to prevent issuance of unnecessary notification. In a case where novice doctors are targeted, an increase in detection sensitivity makes a lesion easier to be detected, whereby it is possible to prevent a doctor from overlooking the lesion. However, what kind of lesion about which notification is desired to be made largely depends on a user's preference. In a case where the threshold has been changed, it is difficult to preliminarily grasp how a detection result changes. Hence, it is not easy to make a sensitivity setting that reflects the user's preference.

In a case where a trained model is generated for each organ, generated are a trained model that is suited to detection of a lesion in the stomach and a trained model that is suited to detection of a lesion in the intestine. By switching the trained model to be used depending on an organ serving as an observation target, detection accuracy is expected to increase. However, merely switching the trained model depending on a part cannot sufficiently reflect the user's preference. This is because, even in a case where an identical part is observed, what kind of lesion about which notification is desired to be made is different depending on a user.

The method in accordance with International Publication No. 2019/087791 is to compare performance of a plurality of classifiers to determine whether or not to update a classifier. However, the user's preference is not reflected on determination about whether or not the performance is improved. In addition, the user cannot grasp how the detection result specifically changes before and after the updating. The method in accordance with International Publication No. 2018/180573 is to display images before and after updating of image processing software. International Publication No. 2018/180573 relates to a technique of simultaneously displaying a plurality of images as processing results, and never discloses a classifier that detects a region of interest from an image, let alone a method of performing display regarding performance of the classifier.

FIG. 1 is a diagram illustrating a configuration of a diagnosis support system 100 in accordance with the present embodiment. The diagnosis support system 100 includes a classification section 110, a performance information processing section 120, and a user's selection receiving section 130. However, a configuration of the diagnosis support system 100 is not limited to that illustrated in FIG. 1. Part of the configuration may be omitted, and various modification can be made, such as addition of another configuration. For example, the diagnosis support system 100 may include a configuration of a processing device 330, which will be described later with reference to FIG. 2, or may include a learning section 210, which will be described later with reference to FIG. 6.

The classification section 110 is capable of outputting a plurality of detection results based on a plurality of classifier candidates that outputs mutually different detection results when detecting the region of interest from an input image. The input image in the present embodiment is, specifically, an in-vivo image in which the living body is captured. Note that the region of interest in the present embodiment is a region in which the order of priority in observation for the user is relatively higher than that in other regions. In a case where the user is a doctor who makes a diagnosis or performs a treatment, the region of interest corresponds to, for example, a region that shows a lesion portion. Note that if a target the doctor wants to observe is bubbles or residues, the region of interest may be a region that shows a portion of the bubbles or a portion of the residues. That is, while a target to which the user should pay attention is different depending on a purpose of observation, a region where the order of priority in observation for the user is relatively higher than that in the other regions is the region of interest. The following description will be given of an example in which the region of interest is a region corresponding to a lesion.

A plurality of classifier candidates mentioned herein is a plurality of mutually different trained models that can be acquired by the diagnosis support system 100. The plurality of trained models may be stored in a storage section of the diagnosis support system 100 or may be acquired from an external device with use of a communication section. The storage section and the communication section are not illustrated. The classification section 110 is capable of switching the detection result as an output by switching which of the plurality of trained models the classification section 110 follows to operate. As described later with reference to FIGS. 9 and 10, the classification section 110 is not prevented from outputting a plurality of detection results simultaneously. As described later with reference to FIG. 8, the classifier candidate is not limited to the trained model alone, and may be a combination of at least one of preprocessing or post-processing and the trained model.

The performance information processing section 120 performs a process of displaying performance information serving as information regarding performance of a plurality of classifier candidates. For example, the performance information processing section 120 is a processor that performs display control, and performs a process of generating a display image and control of causing a display section to display the display image. Details of a screen that displays the performance information will be described later with reference to FIGS. 9 to 14. Note that the performance information processing section 120 may perform a process of generating the performance information or perform a process of acquiring the performance information generated in an external device.

The user's selection receiving section 130 receives a selection operation performed by the user as a user's selection. Specifically, the user's selection receiving section 130 receives the user's selection for selecting at least one of the plurality of classifier candidates as a classifier serving as an output target. The user's selection receiving section 130 is, for example, a processor that controls an operation interface, which is not illustrated. As the operation interface, various kinds of interfaces, such as a mouse, a keyboard, a touch panel, a button, a lever, and a knob, can be used.

The classification section 110 in accordance with the present embodiment outputs a detection result of a classifier selected by the user's selection. In accordance with the method of the present embodiment, the diagnosis support system 100 presents performance information of a plurality of classifiers to the user and then outputs a detection result of the region of interest using the classifier selected by the user. Since the user sees the performance information and then selects the classifier, he/she is able to select the classifier that is suited to his/her preference. Hence, the diagnosis support system 100 is capable of outputting the detection result that is suited to the user's preference.

Note that the diagnosis support system 100 in accordance with the present embodiment is composed of the following hardware. The hardware can include at least one of a circuit that processes a digital signal or a circuit that processes an analog signal. For example, the hardware can include one or more circuit devices mounted on a circuit board, or one or more circuit elements. The one or more circuit devices are, for example, integrated circuits (ICs), field-programmable gate array (FPGA) circuits, or the like. The one or more circuit elements are, for example, resistors, capacitors, or the like.

Each section of the diagnosis support system 100 may be implemented by the following processor. The diagnosis support system 100 includes a memory that stores information, and a processor that operates based on the information stored in the memory. The information is, for example, a program, various kinds of data, and the like. The processor includes hardware. Note that various kinds of processors such as a central processing unit (CPU), a graphics processing unit (GPU), and a digital signal processor (DSP) can be used. The memory may be a semiconductor memory such as a static random access memory (SRAM) and a dynamic random access memory (DRAM). The memory may be a register. The memory may be a magnetic storage device such as a hard disk drive (HDD). The memory may be an optical storage device such as an optical disk device. For example, the memory stores a computer-readable instruction. The instruction is executed by the processor, whereby functions of sections of the diagnosis support system 100 is implemented as processing. The diagnosis support system 100 includes, for example, the classification section 110, the performance information processing section 120, and the user's selection receiving section 130, which are illustrated in FIG. 1. The instruction mentioned herein may be an instruction of an instruction set that is included in a program, or may be an instruction that instructs a hardware circuit included in the processor to operate. Furthermore, all or part of the sections of the diagnosis support system 100 can be implemented by cloud computing, and each processing, which will be described later, can be executed on the cloud computing.

Figure 2:
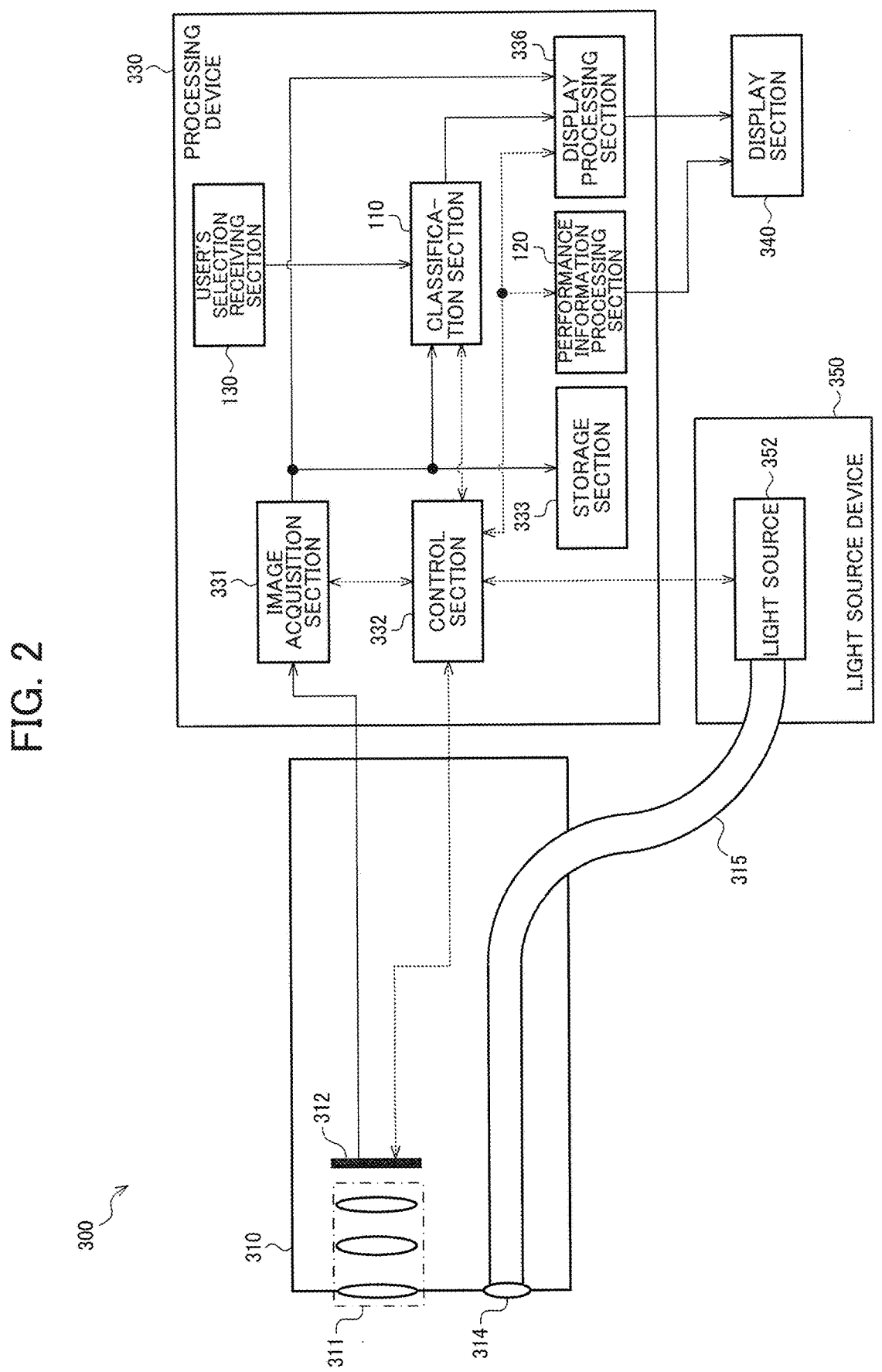
FIG. 2 illustrates a configuration example of an endoscope system including the diagnosis support system.

The diagnosis support system 100 in accordance with the present embodiment, for example, may be included in an endoscope system 300. FIG. 2 is a diagram illustrating a configuration example of the endoscope system 300 including the diagnosis support system 100.

The endoscope system 300 includes an insertion section 310, a processing device 330, a display section 340, and a light source device 350. However, the configuration of the endoscope system 300 is not limited to that illustrated in FIG. 2. The configuration can be modified in various manners, such as omission of part of the configuration and addition of another configuration.

The light source device 350 includes a light source 352 that emits illumination light. The light source 352 may be a xenon light source, a light emitting diode (LED), or a laser light source. Alternatively, the light source 352 may be another light source, and a light emission method is not limited.

The insertion section 310 includes an objective optical system 311, an image sensor 312, an illumination lens 314, and a light guide 315. The light guide 315 guides illumination light emitted from the light source 352 to a leading end of the insertion section 310. The illumination lens 314 emits illumination light guided by the light guide 315 onto an object. The objective optical system 311 receives reflected light from the object and forms an image as an object image. The objective optical system 311 includes, for example, a focus lens, and may be capable of changing a position at which the object image is formed in accordance with a position of the focus lens. For example, the insertion section 310 includes an actuator that drives the focus lens based on control by a control section 332. The actuator is not illustrated. The control section 332 performs autofocus (AF) control.

The image sensor 312 receives light from the object having passed through the objective optical system 311. The image sensor 312 may be a monochrome sensor, or may be an element having a color filter. The color filter may be a filter in a well-known Bayer's arrangement, a complementary color filter, or another filter. The complementary color filter includes filters in respective colors of cyan, magenta, and yellow.

The processing device 330 performs image processing and control of the whole system. The diagnosis support system 100 in accordance with the present embodiment is, for example, included in the processing device 330. The processing device 330 includes the classification section 110, the performance information processing section 120, the user's selection receiving section 130, an image acquisition section 331, the control section 332, a storage section 333, and a display processing section 336.

The processing device 330 is, for example, one device that is connected to the insertion section 310 via a connector, but is not limited thereto. For example, a configuration of part or the whole of the processing device 330 may be structured by another information processing device such as a personal computer (PC) and a server system that can be connected via a network. For example, the processing device 330 may be implemented by cloud computing. The network mentioned herein may be a private network such as an intranet, or may be a public telecommunication network such as the Internet. In addition, the network may be a wired network or a wireless network. That is, the diagnosis support system 100 may also be implemented as one device or implemented by distributed processing by a plurality of devices.

The image acquisition section 331 acquires image data captured by the image sensor 312. The image acquisition section 331 performs analog/digital (A/D) conversion for converting analog signals, which are sequentially output from the image sensor 312, to digital images, and performs a correction process of various kinds on image data after the A/D conversion. Note that the image sensor 312 is provided with an A/D conversion circuit, and the A/D conversion in the image acquisition section 331 may be omitted. Examples of the correction process mentioned herein include a color matrix correction process, a structure enhancement process, a noise reduction process, and automatic gain control (AGC). The image acquisition section 331 may perform another correction process such as a white balance process. The image acquisition section 331 outputs the processed image to the classification section 110 as an input image. In addition, the image acquisition section 331 outputs the processed image to the display processing section 336.

The performance information processing section 120 performs a process of displaying the performance information. Specifically, the performance information processing section 120 performs a process of generating a display screen for displaying the performance information and causing the display section 340 to display the display screen.

The user's selection receiving section 130 receives operation information representing an operation input to an operating section. The operating section mentioned herein is for the user to perform various operations on the endoscope system 300, and is implemented by various kinds of buttons, a graphical user interface (GUI), or the like. The operating section may include, for example, a knob for operating bending of the leading end of the insertion section 310, a button for controlling the start/end of AF, and the like. The user's selection receiving section 130 receives the user's selection operation with respect to display of the performance information.

The storage section 333 is a work area for the control section 332, the classification section 110, and the like, and a function thereof can be implemented by a memory such as a static random access memory (SRAM) and a dynamic random access memory (DRAM), an HDD, or the like. The storage section 333 stores, for example, a plurality of trained models that is different in output.

The classification section 110 performs a process for detecting the region of interest from the input image. Specifically, the classification section 110 performs a process of identifying a trained model based on the user's selection that is made regarding display of the performance information and that is received by the user's selection receiving section 130. The classification section 110 operates in accordance with the identified trained model to perform the process of detecting the region of interest from the input image, and thereafter outputs the detection result to the display processing section 336. In addition, the classification section 110 may output a degree of reliability representing a degree of probability of the detected region of interest.

The display processing section 336 performs processing based on the image from the image acquisition section 331 and the detection result from the classification section 110, and performs a process of outputting a processing result to the display section 340. For example, the display processing section 336 may perform a process of adding the detection result from the classification section 110 to the image from the image acquisition section 331, and displaying the image to which the detection result is added.

The control section 332 is connected to each of the classification section 110, the performance information processing section 120, the user's selection receiving section 130, the image sensor 312, the image acquisition section 331, the display processing section 336, and the light source 352, and controls each section.

The display section 340 is, for example, a liquid crystal display, an electro-luminescence (EL) display, or the like.

Figure 3:
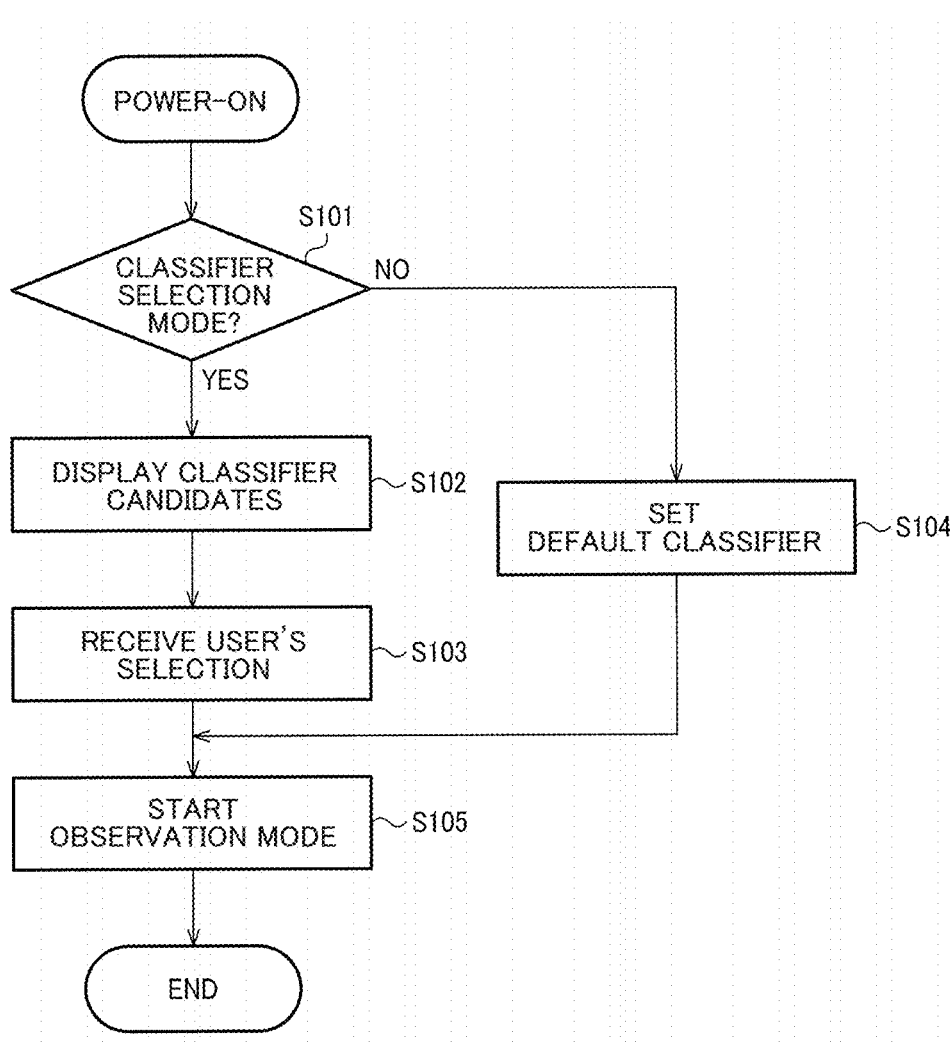
FIG. 3 is a flowchart describing processing in the diagnosis support system.

FIG. 3 is a flowchart describing the outline of processing of the diagnosis support system 100 in accordance with the present embodiment. This processing is started, for example, by power-on of the diagnosis support system 100. For example, when each section of the endoscope system 300 including the diagnosis support system 100 transitions to an operable state, the following processing is executed.

First, in step S101, whether or not an operation mode of the diagnosis support system 100 is a classifier selection mode is determined. Processing in step S101 may be performed by the classification section 110 or may be performed by the control section 332. The classifier selection mode is a mode for displaying the performance information to receive the user's selection of the classifier used for outputting of the detection result.

In a case of YES in step S101, in step S102, the performance information processing section 120 performs a process of displaying the performance information of classifier candidates. In step S103, the user's selection receiving section 130 performs a process of receiving the user's selection for selecting any of the classifier candidates. The classification section 110 identifies the classifier candidate selected by the user as the classifier used for outputting of the detection result.

In a case of NO in step S101, the user's selection receiving section 130 does not receive the user's selection for selecting a classifier. In this case, for example, the classification section 110 identifies a default classifier candidate as the classifier used for outputting of the detection result.

After the processing in step S103 or step S104, in step S105, the diagnosis support system 100 starts an operation in an observation mode. The observation mode is a mode for inserting the insertion section 310 into the inside of a living body to capture an in-vivo image. The observation mode can be referred in other words to as a mode in which the user such as a doctor observes the inside of the living body of a patient based on the in-vivo image. In the observation mode, the image acquisition section 331 sequentially acquires time-series in-vivo images captured by the image sensor 312, and outputs the in-vivo images to the classification section 110. The classification section 110 inputs the in-vivo images to the classifier identified in step S104 or step S105, and acquires and outputs the detection result of the region of interest.

The method in accordance with the present embodiment may be implemented as a diagnosis support method. The diagnosis support method includes acquiring the performance information serving as information regarding performance of the plurality of classifier candidates that outputs mutually different detection results when detecting the region of interest from the input image, presenting the acquired performance information to the user, receiving the user's selection for selecting at least one of the plurality of classifier candidates as the classifier serving as the output target, and outputting the detection result of the classifier candidate selected by the user's selection.

The method in accordance with the present embodiment may be applied to a program that implements processing performed by the diagnosis support system 100. The program can be stored, for example, in an information storage device, which is a computer readable storage medium. The information storage medium is implemented by, for example, an optical disk, a memory card, an HDD, or a semiconductor memory. The semiconductor memory is, for example, a read-only memory (ROM). The diagnosis support system 100 performs various kinds of processing in accordance with the present embodiment based on the program stored in the information storage device. That is, the information storage device stores the program for causing the computer to function as each section of the diagnosis support system 100. The computer is a device provided with an input device, a processing section, a storage section, and an output section. Specifically, the program in accordance with the present embodiment is a diagnosis support program for causing the computer to execute each step, which will be described later with reference to FIG. 3.

The diagnosis support program causes the computer to acquire the performance information serving as information regarding performance of the plurality of classifier candidates that outputs mutually different detection results when detecting the region of interest from the input image, present the acquired performance information to the user, receive the user's selection for selecting at least one of the plurality of classifier candidates as the classifier serving as the output target, and output the detection result of the classifier candidate selected by the user's selection. For example, each section of the diagnosis support system 100 in accordance with the present embodiment is implemented as a module of a program that operates on a processor. The processor includes hardware. The classification section 110 is implemented as an image processing module for detecting the region of interest from the input image based on the classifier. The performance information processing section 120 is implemented as a display control module for displaying the performance information. The user's selection receiving section 130 is implemented as an interface control module for receiving operation information indicating the user's selection.

2. Example of a Plurality of Classifier Candidates

As described above, the diagnosis support system 100 in accordance with the present embodiment is capable of outputting a plurality of detection results based on the plurality of classifier candidates. An example of the plurality of classifiers that outputs mutually different detection results will be described in detail below. Note that the following description will be given of an example in which the classifier includes a trained model acquired by machine learning. However, the classifier may be an image processing algorithm or the like generated without using the machine learning.

2.1 Example of Trained Model

The classifier in accordance with the present embodiment is, for example, a trained model that performs a process of detecting a lesion from an input image, and that outputs a detection result. The machine learning in accordance with the present embodiment is, for example, supervised learning. One piece of learning data used for the machine learning is data in which a piece of input data and a correct label corresponding to the piece of input data are associated with each other. The input data is a learning image. The correct label is information that identifies the lesion in the learning image. The correct label may be information that identifies the presence/absence of the lesion, a position of the lesion, and a size of the lesion. The classifier in accordance with the present embodiment may classify the lesion. The correct label in this case includes information that identifies a result of classifying the lesion. The result of classification is, for example, a result of classification in accordance with a degree of malignancy of the lesion. The correct label is, for example, a result of annotation added by a user who has expert knowledge, such as a doctor.

The outline of the machine learning is now described. The following description is given of the machine learning using a neural network, but the method in accordance with the present embodiment is not limited thereto. In the present embodiment, for example, machine learning using another model such as a support vector machine (SVM) may be performed, and machine learning using a method that has developed from various methods such as the neural network and the SVM may be performed.

Figures 4A, 4B:
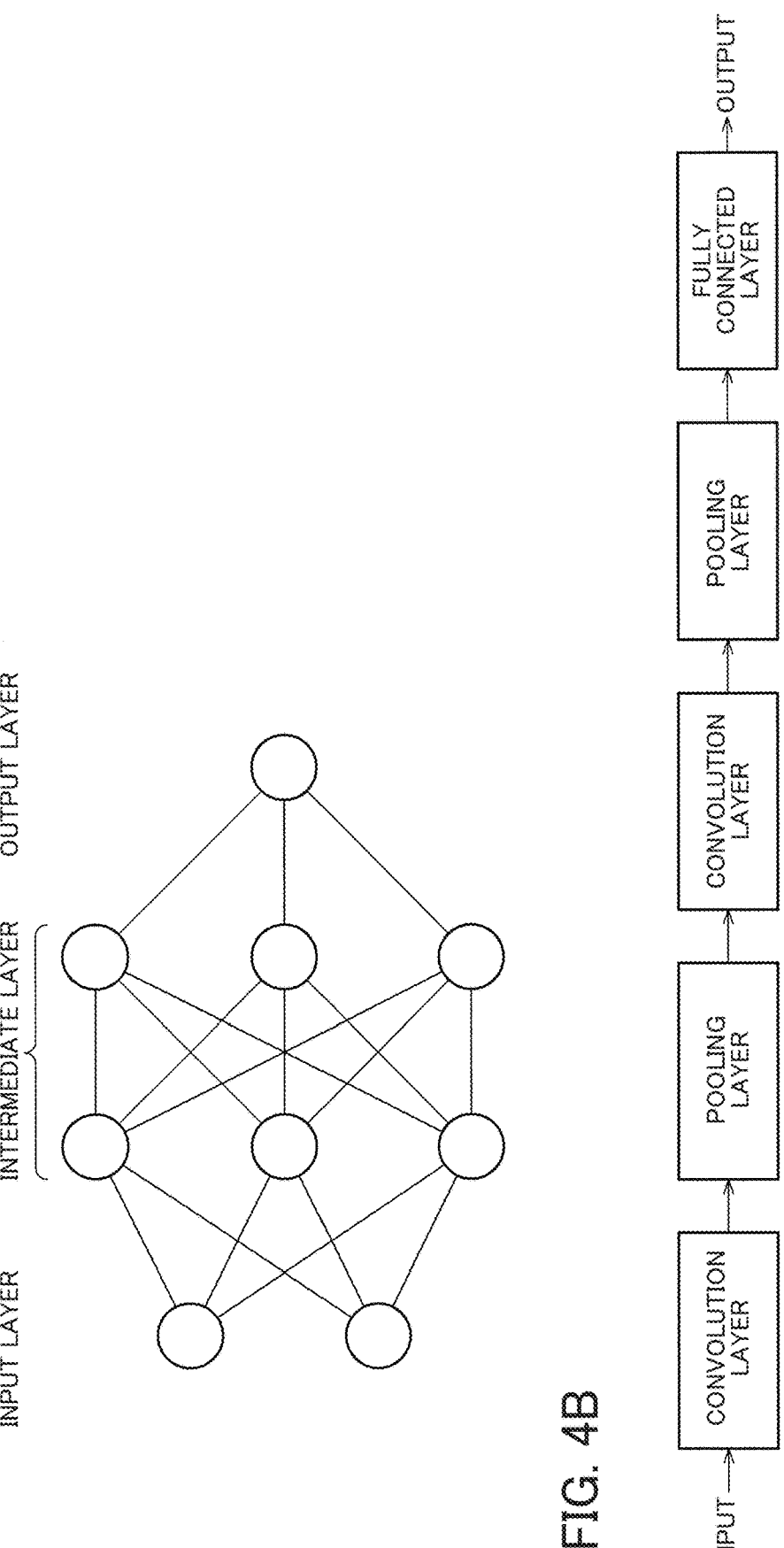
FIGS. 4A and 4B are diagrams for describing a neural network.

FIG. 4A is a schematic diagram for describing the neural network. The neural network includes an input layer that takes input data, an intermediate layer that executes calculation based on an output from the input layer, and an output layer that outputs data based on an output from the intermediate layer. While FIG. 4A exemplifies a network having the intermediate layer composed of two layers, the intermediate layer may be composed of one layer, or three or more layers. In addition, the number of nodes included in each layer is not limited to that in the example of FIG. 4A, and can be modified in various manners. Note that in consideration of accuracy, learning in accordance with the present embodiment is preferably performed using deep learning using a multi-layer neural network. The multi-layer mentioned herein means four or more layers in a more limited sense.

As illustrated in FIG. 4A, a node included in a given layer is connected to a node in an adjacent layer. A weight coefficient is assigned between connected nodes. Each node multiplies an output from a node in a former stage by the weight coefficient and obtains a total value of results of multiplication. Furthermore, each node adds a bias to the total value and applies an activation function to a result of addition to obtain an output from the node. This processing is sequentially executed from the input layer to the output layer, whereby an output from the neural network is obtained. Note that as the activation function, various kinds of functions such as a sigmoid function and a rectified linear unit (ReLU) function are known, and a wide range of these functions can be applied in the present embodiment.

The learning in the neural network is a process of determining an appropriate weight coefficient. The weight coefficient mentioned herein includes a bias. The following description is given of an example in which a process of generating the trained model is performed in a learning device. The learning device may be a learning section 210 or a learning device 220, which will be described later with reference to FIG. 6.

The training device inputs input data out of learning data to the neural network and performs calculation in a forward direction using a weight coefficient at this time to obtain an output. The learning device calculates an error function based on the output and the correct label out of the learning data. The learning device updates the weight coefficient to make the error function smaller. In updating the weight coefficient, for example, backpropagation to update the weight coefficient from the output layer to the input layer can be utilized.

The neural network may be, for example, a convolutional neural network (CNN). FIG. 4B is a schematic diagram for describing the CNN. The CNN includes a convolution layer that performs convolution calculation and a pooling layer. The convolution layer is a layer that performs a filter process. The pooling layer is a layer that reduces a size in a vertical direction and a size in a lateral direction to perform pooling calculation. In the example illustrated in FIG. 4B, the CNN is a network that causes each of the convolution layer and the pooling layer to perform calculation multiple times, thereafter causes a fully connected layer to perform calculation, and thereby obtain an output. The fully connected layer is a layer that performs a calculation process in a case where all nodes included in the former layer are connected to corresponding nodes in the given layer, and the calculation process corresponds to calculation in each layer described above with reference to FIG. 4A. Note that also in a case where the CNN is used, although not illustrated in FIG. 4B, the calculation process with the activation function is performed similarly to the case in FIG. 4A. Various configurations of the CNN have been known, and a wide range of these configurations are applicable to the present embodiment.

Also in the case where the CNN is used, a procedure of processing is similar to that illustrated in FIG. 4A. That is, the learning device inputs input data, out of the learning data, to the CNN, and performs a filter process or pooling calculation using filter characteristics at that time to obtain an output. The learning device calculates the error function based on the output and the correct label, and updates the weight coefficient including the filter characteristics to make the error function smaller. For example, the backpropagation can be utilized also when the weight coefficient of the CNN is updated.

Figure 5:
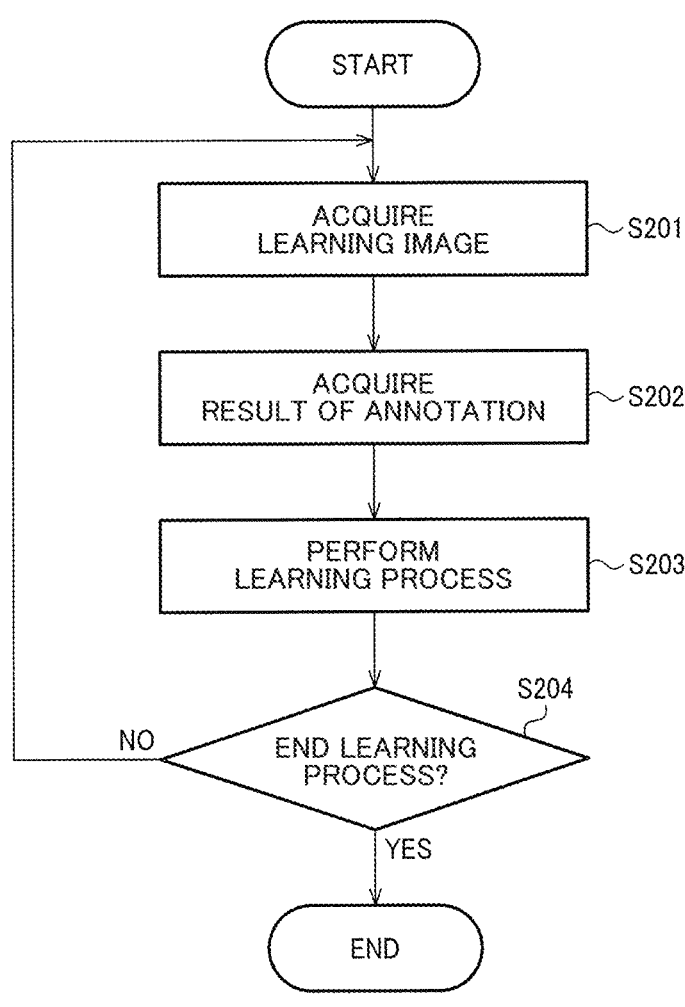
FIG. 5 is a flowchart describing a learning process.

FIG. 5 is a schematic diagram for describing learning processing in the neural network. First, in steps S201 and S202, the learning device acquires the learning image and the correct label associated with the learning image. For example, the learning device acquires multitudes of pieces of data in which the learning image and the correct label are associated with each other, and stores the data as learning data. The processing in each of steps S201 and S202 is, for example, a process of reading out one piece of data out of the learning data.

In step S203, the learning device performs a process of calculating an error function. Specifically, the learning device inputs the learning image to the neural network and performs calculation in the forward direction based on a weight coefficient at this time. The learning device then calculates the error function based on a process of comparing a calculation result and the correct label with each other. Furthermore, in step S203, the learning device performs a process of updating the weight coefficient to make the error function smaller. The backpropagation or the like can be utilized for this process, as described above. The processing in steps S201 to S203 corresponds to a one-time learning process based on one piece of learning data.

In step S204, the learning device determines whether to end the learning process. For example, the learning device may retain part of multitudes of learning data as evaluation data. The evaluation data is data for checking accuracy of a learning result, and data that is not used for updating the weight coefficient. In a case where a rate of correct answers in an estimation process using the evaluation data exceeds a predetermined threshold, the learning device ends the learning process.

In a case of NO in step S204, the processing returns to step S201, and the learning process based on subsequent learning data continues. In a case of YES in step S204, the learning process ends. The learning device transmits information of the generated trained model to the diagnosis support system 100. In the example illustrated in FIG. 2, the information of the trained model is stored in the storage section 333. Various kinds of methods for the machine learning such as batch learning and mini-batch learning have been known, and a wide range of these methods are applicable to the present embodiment.

2.2 Original Classifier Candidate and Customized Classifier Candidate

A plurality of classifier candidates that outputs different detection results may include an original classifier candidate and a customized classifier candidate. The original classifier candidate is, for example, a classifier candidate that comes with the diagnosis support system 100 when the diagnosis support system 100 is provided. For example, the original classifier candidate is a classifier candidate that is generated by a manufacturer that provides the diagnosis support system 100 or the like. For example, in a case where the diagnosis support system 100 is utilized in a plurality of hospitals, the original classifier candidate is provided in common to the plurality of hospitals.

Meanwhile, the customized classifier candidate is a classifier candidate generated by a user based on an image acquired by the user. For example, in each hospital, iv-vivo images are acquired and accumulated using the endoscope system 300. The customized classifier candidate is generated by machine learning using each in-vivo image as the learning image. Hence, the customized classifier candidate is a classifier candidate that is different depending on a hospital.

Figure 6:
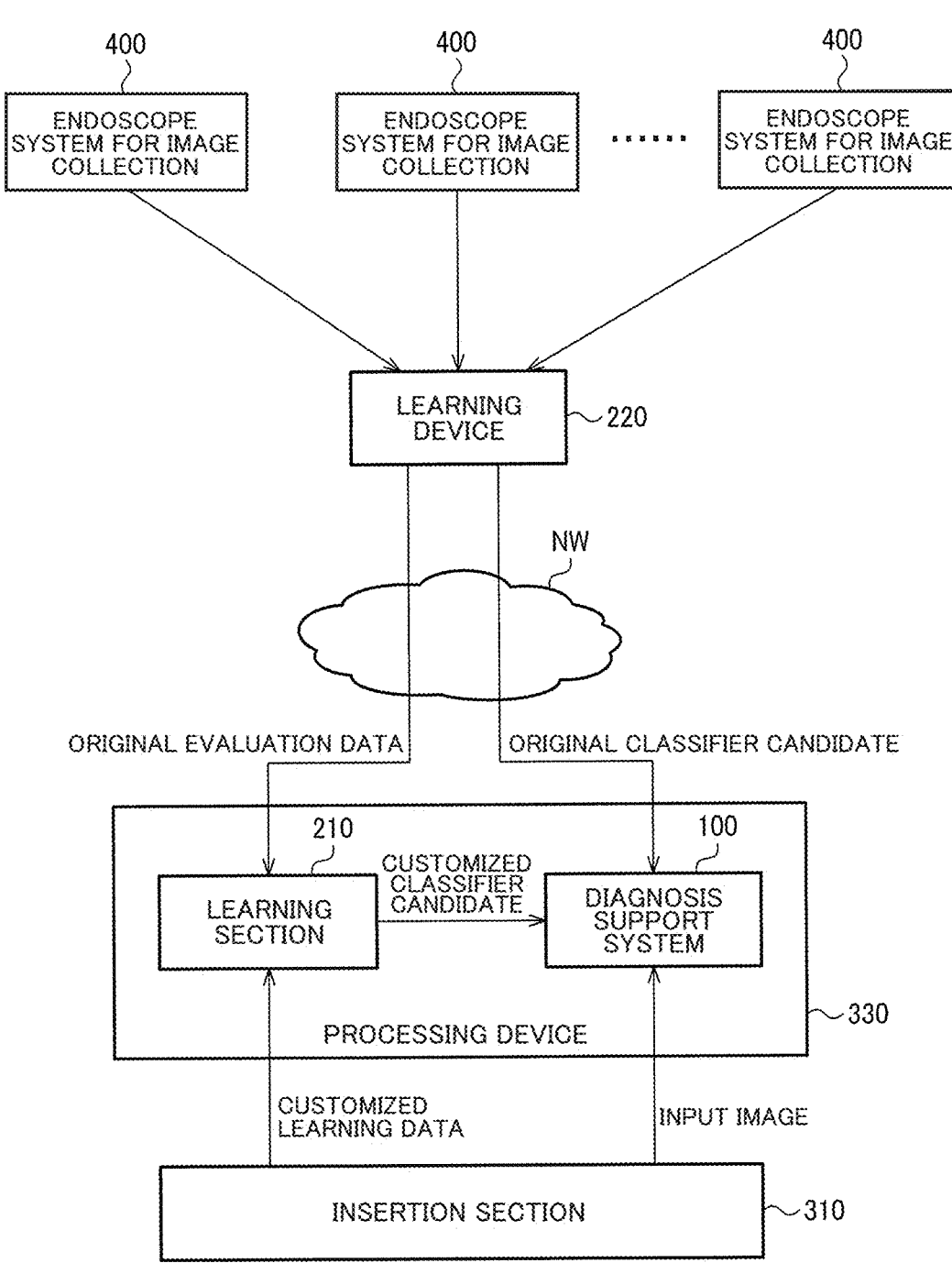
FIG. 6 illustrates an example of a method of acquiring an original classifier and a customized classifier.

FIG. 6 is a diagram for describing a configuration example of a system using the original classifier candidate and the customized classifier candidate. The system includes the insertion section 310, the processing device 330, the learning device 220, and an endoscope system for image collection 400. The processing device 330 includes the diagnosis support system 100 and the learning section 210. Note that a configuration of the system is not limited to the configuration illustrated in FIG. 6. The configuration can be modified in various manners such as partial omission of constituent elements and addition of another constituent element. The processing device 330 is the processing device 330 illustrated in FIG. 2, and may be implemented as one device or implemented by distributed processing by a plurality of devices. The insertion section 310 and the processing device 330 correspond to the endoscope system 300 illustrated in FIG. 2.

The endoscope system for image collection 400 captures a plurality of in-vivo images for creating the original classifier candidate. The learning device 220 acquires a pair of the learning image captured by the endoscope system for image collection 400 and a result of annotation added to the learning image as the learning data used for the machine learning. The learning data includes original learning data and original evaluation data. The learning device 220 performs the machine learning based on the original learning data to generate a trained model corresponding to the original classifier candidate. The learning device 220 evaluates the generated trained model based on the original evaluation data. The trained model is, for example, a model that performs an inference process in accordance with deep learning, as described above. The learning device 220 transmits the generated trained model to the diagnosis support system 100 via a network NW. The network NW mentioned herein may be a public telecommunication network such as the Internet or a private network.

Meanwhile, the endoscope system 300 captures a plurality of in-vivo images using the insertion section 310. The endoscope system 300 acquires a correct label corresponding to each of the plurality of in-vivo images, and stores data in which the in-vivo image and the correct label are associated with each other as customized learning data in the storage section 333. The learning section 210 performs the processing illustrated in FIG. 5 based on the customized learning data to generate a trained model corresponding to the customized classifier candidate. The learning section 210 transmits the generated trained model to the diagnosis support system 100.

This allows the diagnosis support system 100 to execute a detection process based on the original classifier candidate and the customized classifier candidate that are different in learning data.

Figure 7A:
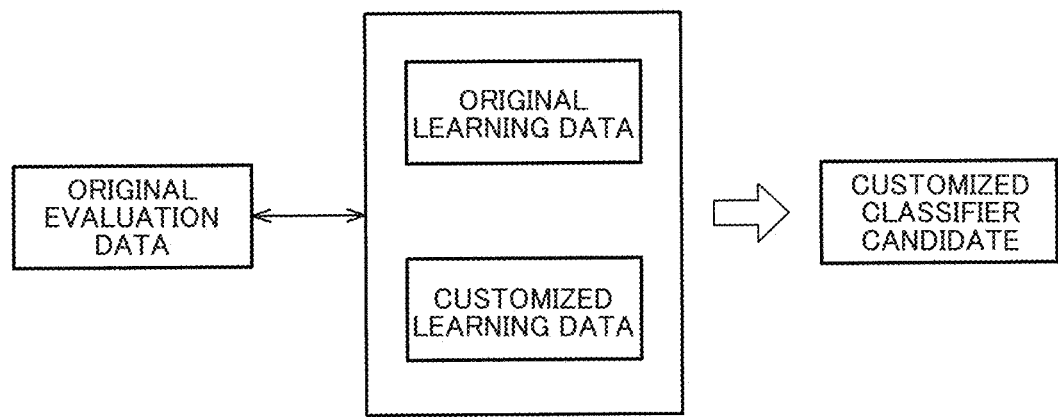
FIGS. 7A to 7C each illustrate an example of data used for generation and evaluation of the customized classifier.
Figure 7B:
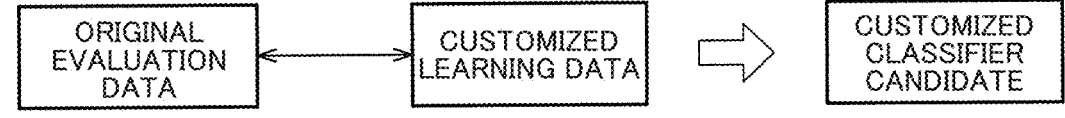
Figure 7C:
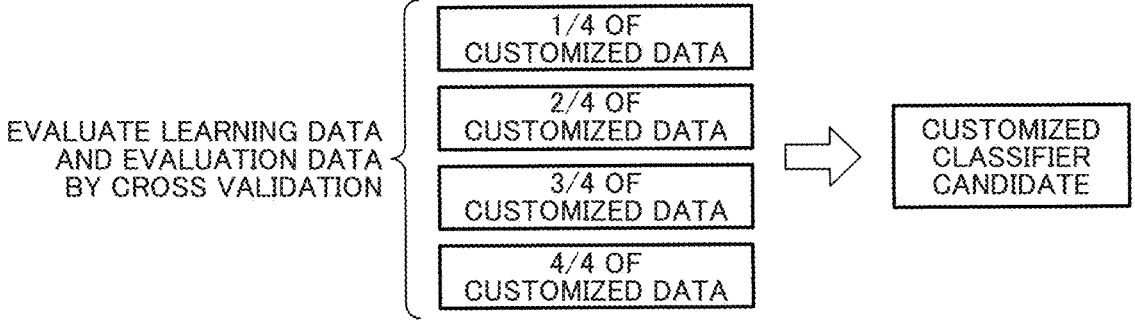

FIGS. 7A to 7C are diagrams each illustrating a method of generating the customized classifier candidate based on the customized image data. As illustrated in FIG. 7A, the customized classifier candidate may be generated based on both the original learning data and the customized learning data. Then, a customized classifier is evaluated based on the original evaluation data. Alternatively, as illustrated in FIG. 7B, the customized classifier candidate may be generated based on the customized learning data. In an example illustrated in FIG. 7B, the customized classifier candidate is evaluated using the original evaluation data similarly to an example illustrated in FIG. 7A.

Alternatively, as illustrated in FIG. 7C, the customized classifier candidate may be generated and evaluated based on the customized learning data. For example, the customized learning data is divided into four pieces of customized learning data. The learning section 210 repeats a process of generating the customized classifier candidate based on three pieces of customized learning data out of the four pieces of customized learning data, and evaluating the generated customized classifier candidate based on the remaining one piece of customized learning data, four times. Execution of cross-validation enables appropriate generation and evaluation of the customized classifier candidate based on the customized learning data.

As described above, the machine learning is only required to be performed on the customized classifier candidate using the customized learning data that is not used for learning of the original classifier candidate, and whether or not the original learning data is used and how to evaluate the customized classifier candidate can be modified in various manners. In any methods, with use of the customized learning data, a detection result of the customized classifier candidate is expected to be different from a detection result of the original classifier candidate.

As described above, the plurality of classifier candidates in accordance with the present exemplary embodiment may include the original classifier candidate and the customized classifier candidate created by the user. This allows the user to add his/her original classifier candidate.

As described above, the method in accordance with the present embodiment is to output a detection result for the region of interest that reflects the user's preference. However, it is not realistic to create an exhaustive original classifier candidate that satisfies a preference of every user. In this regard, allowing the user to add a classifier candidate can increase a probability for the presence of a classifier candidate that is suited to the user's preference.

The customized classifier candidate is created based on the machine learning using learning images including an image held by the user, as illustrated in FIGS. 7A to 7C. The image held by the user is, for example, an in-vivo image that has been previously set by the user as a target of observation or treatment. Hence, it is presumed that the user has many opportunities for performing observation targeting at a region of interest of a similar kind. Use of the image held by the user in learning of the customized classifier candidate enables creation of the classifier candidate having a higher probability for being suited to the user's preference.

2.3 Difference Between Models

The plurality of classifier candidates is not limited to those that are different in learning data used for learning as described above. For example, the plurality of classifier candidates may be classifier candidates whose models are mutually different. The model mentioned herein represents, for example, the configuration of the neural network illustrated in FIGS. 4A and 4B. The models being different specifically means that at least one of pieces of information that determines characteristics of the neural network is different. Examples of the information that determines characteristics include the number of intermediate layers, the number of nodes included in each layer, a connection relationship between a node in a given layer and a node in a next layer, and an activation function. For example, as a CNN that detects a given object, various kinds of models such as a Faster Region-based CNN (Faster R-CNN), You only Look Once (YOLO), and a Single Shot Detector (SSD), have been known. The two models being different means, for example, that one of the two models is the YOLO, and the other thereof is the SSD.

As described above, in a case where the learning data is different among a plurality of trained models, different trained models are generated even from an identical model. Specifically, a calculation algorithm in the forward direction is identical but weight coefficient information is different from each other, whereby the plurality of trained models that outputs different detection results with respect to an identical input image is generated.

In a case where models are different from each other, different trained models are generated even if the learning data is identical. Specifically, since calculation algorithms in the forward direction are different from each other in the first place, the plurality of trained models that outputs different detection results from the identical input image is generated.

As a matter of course, the plurality of classifier candidates may be different in both learning data and model. For example, the original classifier candidate and the customized classifier candidate described above may be different not only in learning data used for learning but also in the model itself.

Note that "the detection result being different" in the present embodiment means that at least one of the learning data or the model is only required to be different, as described above. In other words, "the detection result being different" means that the difference in calculation algorithm in the forward direction or weight coefficient information differentiates processing to be executed in the input image. Hence, depending on a specific trained model or an input image, incidental coincidence of detection results from the plurality of classifier candidates is not excluded.

2.4 Pre-Processing and Post-Processing

As described above, the classifier candidate is the trained model in a limited sense. That is, the storage section stores information regarding the trained model. The classification section 110 serving as a processor operates in accordance with an instruction from the trained model read out from the storage section to perform the process of detecting the region of interest from the input image.

Calculation in accordance with the trained model in the classification section 110, that is, calculation for outputting output data based on input data, may be executed by software, or may be executed by hardware. In other words, product-sum calculation executed in each node in FIG. 4A, or a filter process or the like executed in the convolution layer of the CNN may be executed by software. Alternatively, the above-mentioned calculation may be executed by a circuit device such as the FPGA circuit. Still alternatively, the above-mentioned calculation may be executed by software and hardware in combination. In this manner, operations of the classification section 110 in accordance with an instruction from the trained model can be implemented in various manners. For example, the trained model includes an inference algorithm, and a weight coefficient used in the inference algorithm. The inference algorithm is an algorithm for performing filter calculation or the like based on input data. In this case, both the inference algorithm and the weight coefficient are stored in the storage section, and the classification section 110 may read out the inference algorithm and the weight coefficient to perform an inference process with software. The storage section is, for example, the storage section 333 of the processing device 330, but another storage section may be used. Alternatively, the inference algorithm may be implemented by the FPGA circuit or the like, and the storage section may store the weight coefficient. Still alternatively, the inference algorithm including the weight coefficient may be implemented by the FPGA circuit or the like. In this case, the storage section that stores information of the trained model is, for example, a built-in memory of the FPGA circuit.

The classifier candidate in accordance with the present embodiment is, for example, the trained model itself. For example, the detection result of the classifier candidate corresponds to an output when the input image is input to the trained model. However, the classifier candidate is not limited to the trained model alone.

Figure 8:
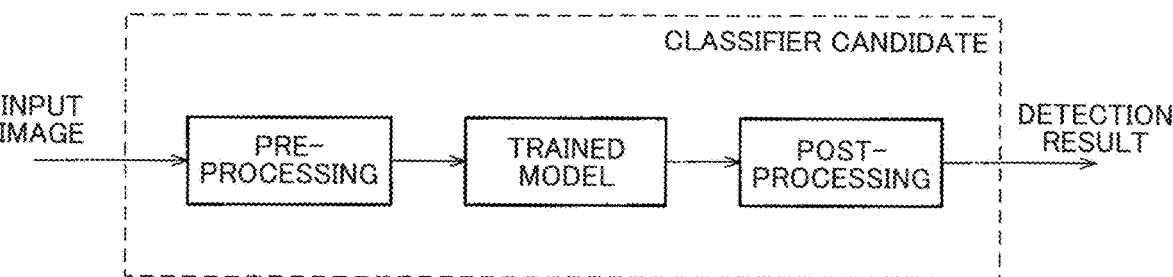
FIG. 8 is a diagram for describing processing performed in a classifier candidate.

FIG. 8 is a diagram for processing in the classifier candidate. As illustrated in FIG. 8, in the classifier candidate, some kind of pre-processing is performed on the input image, and a result of the pre-processing is input to the trained model. In addition, a result of some kind of post-processing performed on the output of the trained model is output as the detection result. Note that either the pre-processing or the post-processing in FIG. 8 may be omitted.

For example, a flat lesion has few characteristics such as edges, and is likely to be buried in noise. In this case, execution of pre-processing for integrating input images in a plurality of frames reduces noise, and can thereby increase accuracy of detecting a lesion. However, since there is a need for integrating the plurality of frames, there occurs a time lag until the detection result is output, and a processing load increases. In this manner, there is a trade-off relationship between accuracy and time when the lesion is detected, and which of settings is better depends on the user's preference.

Hence, the plurality of classifier candidates in accordance with the present embodiment may include a plurality of classifiers whose trained models are identical and that have been subjected to different kinds of pre-processing. In the above-mentioned example, a first classifier candidate inputs input images to the trained model without execution of frame integration. A second classifier candidate executes the frame integration of input images in a predetermined number of frames as the pre-processing, and inputs images after the pre-processing to the trained model. This enables generation of the plurality of classifier candidates based on one trained model.

Additionally, on the condition that a lesion that is determined to be identical is consecutively detected in the predetermined number or more frames, the endoscope system 300 outputs a detection result regarding the lesion. This is because, since such a lesion as that appears only for a short period of time and soon disappears from a screen is excluded from a display target, it is possible to prevent frequent change of a display screen. Meanwhile, displaying such a lesion as that appears only for a short period of time and soon disappears from the screen on purpose enables notification of presence of the lesion that is easily overlooked to the user.

Hence, the plurality of classifier candidates in accordance with the present embodiment may include a plurality of classifiers whose trained models are identical and that have been subjected to different post-processing. In the case of the above-mentioned example, the first classifier candidate inputs time-series input images to the trained model to acquire time-series outputs, and performs post-processing for determining whether or not a given lesion is consecutively detected in n1 frames based on the time-series outputs. The second classifier candidate inputs time-series input images to the trained model to acquire time-series outputs, and performs post-processing for determining whether or not the given lesion is consecutively detected in n2 frames based on the time-series outputs. The n1 and the n2 are integers that satisfy $1 < n1 < n2$. This enables generation of the plurality of classifier candidates based on one trained model.

As the pre-processing, a process of extracting a partial region of the input image may be performed. Extracting the partial region can reduce pixels serving as a processing target, and can thereby reduce processing time. In a case where the processing time is maintained, processing time per unit data amount is increased, and thus accuracy can be expected to increase. Also in this case, there is a trade-off relationship between accuracy and time similarly to the above-mentioned example, and which of settings is better depends on the user's preference. Hence, differentiating whether or not pre-processing for trimming the input image or differentiating whether or not a size or position of a region is to be trimmed enables generation of the plurality of classifier candidates based on one trained model.

Additionally, the pre-processing in the classifier candidate is not limited to the above, and can include various kinds of processing performed on the input image before being input to the trained model. Similarly, the post-processing for the classifier candidate is not limited to the above, and can include various kinds of processing performed on the output from the trained model.

Note that the above description has been given assuming that the processing such as the frame integration is the pre-processing or the post-processing that is different from the processing executed in the trained model. However, the trained model that includes the processing such as the frame integration may be generated. For example, the trained model may be a model that receives images in a plurality of frames as input data, performs a noise reduction process corresponding to the frame integration, and then outputs a detection result regarding the region of interest. That is, the pre-processing or the post-processing mentioned herein may be implemented as processing that is different from the processing executed in the trained model, or may be implemented as processing that is executed in the trained model.

As described above, the plurality of classifier candidates is mutually different in processing method with respect to the input image. The processing method mentioned herein corresponds to the pre-processing serving as processing in a former stage of the trained model, the post-processing serving as processing in a subsequent stage of the trained model, or both of the pre-processing and the post-processing. Accordingly, differentiating the processing with respect to the input image enables implementation of the plurality of classifier candidates that outputs different detection results.

For example, as described above, the plurality of classifier candidates may include two or more classifier candidates whose trained models are identical and that have been subjected to different pre-processing or post-processing. The trained model being identical means both the model and the learning data being identical. However, the trained model is not limited to the identical trained model, and the plurality of classifier candidates may include two or more classifier candidates whose trained models are different and that have been subjected to different pre-processing or post-processing. The trained models being different means at least one of the model or the learning data being different.

2.5 Difference in Performance of a Plurality of Classifier Candidates

As described above, the plurality of classifier candidates in accordance with the present embodiment is different in at least one of the learning data, the model, the pre-processing, or the post-processing. This difference enables differentiation of performance of the classifier candidates.

The plurality of classifier candidates in accordance with the present embodiment is, for example, mutually different in detection sensitivity to the presence/absence of the region of interest. The detection sensitivity to the presence/absence represents easiness to detect the region of interest. The sensitivity being high means that the region of interest included in the input image is easily detected, and is less likely to be overlooked. However, in a case where the sensitivity is high, there is a higher probability for false detection of a region that is not the region of interest as the region of interest. In a case where the sensitivity is low, the false detection of the region of interest can be prevented, but there is a higher probability for overlooking of the region of interest. Note that a recall rate, which will be described later, can be utilized as an index representing the detection sensitivity.

This allows outputting of the detection result from the classifier having a detection sensitivity that is suited to user's preference. For example, it is possible to switch display depending on whether the user is a user who thinks that prevention of overlooking is important or a user who thinks that prevention of false detection is important. In a case where the region of interest is detected by the classifier, for example, an object that improves viewability of the region of interest is displayed similarly to FIGS. 9 and 10, which will be described later. In this case, a classifier candidate having a lower sensitivity may possibly be selected for the reason that the user does not like display of multitudes of objects on the display screen.

For example, in a case where the learning data for the first classifier candidate includes multitudes of images regarding the given lesion and the learning data for the second classifier candidate includes not so many images regarding the given lesion, it is assumed that the first classifier candidate has a higher detection sensitivity to the lesion and the second classifier candidate has a lower detection sensitivity to the lesion. In this manner, there occurs a difference in detection sensitivity to the presence/absence of the region of interest due to, for example, a difference in learning data.

Or else, since a processing algorithm in the forward direction is different depending on a model, there exist a model that is suited to detection of a specific structure and a model that is not suited to detection of the structure. Hence, it is also conceivable that there occurs a difference in detection sensitivity to the presence/absence of the region of interest due to a difference in model.

Under a condition that a predetermined number of frames are consecutively detected, a sensitivity to a lesion that is framed out soon decreases. Execution of the frame integration increases a sensitivity to a flat lesion. By trimming part of the input image, the detection sensitivity can be expected to increase by the increased accuracy, but a sensitivity to a lesion in the periphery of the image decreases. In this manner, it is also conceivable that there occurs a difference in detection sensitivity to the presence/absence of the region of interest due to a difference in pre-processing or post-processing.

More specifically, the plurality of classifier candidates is mutually different in at least one of a detection sensitivity to a shape of the region of interest, a detection sensitivity to a size of the region of interest, or a detection sensitivity to a color of the region of interest.

The detection sensitivity to the shape being different means that, for example, when consideration is given to the region of interest having a given shape, a detection sensitivity of the first classifier candidate is higher and a detection sensitivity of the second classifier candidate is lower. Alternatively, in a case where first to n-th shapes, which are n types of shapes (n is an integer of 2 or more), are assumed as shapes of the region of interest, the detection sensitivity to the shape being different means that the first classifier candidate has a relatively higher detection sensitivity to a first shape than the other shapes, and the second classifier candidate has a relatively higher detection sensitivity to a second shape than the other shapes. Still alternatively, when consideration is given to respective detection sensitivities with respect to the first to n-th shapes, tendencies of the detection sensitivities are different between the first classifier candidate and the second classifier candidate. The same applies to the size and the color.

The difference in detection sensitivity to the shape, the size, and the color may be attributed to the learning data, the model, or the pre-processing and the post-processing, similarly to the above-mentioned example. For example, the detection sensitivity to the shape (the size, or the color) can be changed depending on how much amount of images including the region of interest having a specific shape (size, or color) is included in the learning data. In addition, since there exist a model that is suited to detection of the specific shape (size, or color), and a model that is not suited to detection for the specific shape (size, or color), changing the model can change the detection sensitivity to the shape or the like. Execution of a process of adjusting the shape, the size, or the color such as edge enhancement, affine transformation, and color conversion as the pre-processing or the post-processing also can change the detection sensitivity to the shape or the like.

The region of interest may be a region corresponding to a lesion. The plurality of classifier candidates is mutually different in detection sensitivity to medical classification of the lesion. The medical classification represents classification of the lesion from a medical perspective, and may be classification of a lesion type itself, or classification of a degree of malignancy of a specific lesion (disease stage).

For example, as macroscopic classification of gastric cancer, known is a method of classifying the lesion into any of type0 to type5. In addition, regarding type0 superficial cancer, classification such as type0-I as a protruding type, type0-II as a superficial type, type0-III as a depressed type is also known. Besides the above classification, various kinds of classification as medical classification are known, and a wide range of these kinds of classification is applicable to the present embodiment.

The detection sensitivity to the medical classification being different means that, for example, when consideration is given to a given type of the lesion or a given degree of malignancy of the lesion, a detection sensitivity of the first classifier candidate is higher and a detection sensitivity of the second classifier candidate is lower. For example, the first classifier candidate has a higher detection sensitivity to the type0-I, and the second classifier candidate has a lower detection sensitivity to the type0-I. Alternatively, the detection sensitivity to the medical classification being different means that the first classifier candidate has a relatively higher detection sensitivity to a lesion of a first type or a first degree of malignancy, and the second classifier candidate has a relatively higher detection sensitivity to a lesion of a second type or a second degree of malignancy. For example, the first classifier candidate has a higher detection sensitivity to the type0-I than with respect to lesions of other degrees of malignancy, and the second classifier candidate has a higher detection sensitivity to the type0-III than to lesions of other degrees of malignancy. Alternatively, when consideration is given to a relationship among a detection sensitivity to the type0-I, a detection sensitivity to the type0-II, and a detection sensitivity to the type0-III, the relationship is different between the first classifier candidate and the second classifier candidate.

Preparing classifier candidates that are different in performance depending on medical classification allows the user's preference to be more reflected on the detection result. Note that the difference in detection sensitivity to the medical classification may be attributed to the learning data, the model, or the pre-processing and the post-processing, similarly to the above-mentioned example. For example, with use of multitudes of images including the lesion of the given degree of malignancy for machine learning, it is possible to increase a detection sensitivity to the lesion of the given degree of malignancy.

In addition, the plurality of classifier candidates is mutually different in detection result depending on an imaging state when the input image is captured. The imaging state mentioned herein represents, for example, brightness in imaging and a relative positional relationship between the insertion section 310 and the object at the time of the imaging. The positional relationship between the insertion section 310 and the object may be, for example, a distance between the leading end of the insertion section 310 and the object. Alternatively, the relative positional relationship may be an angle between the leading end of the insertion section 310 and the object. The angle is, for example, an angle formed between a surface representing the object and an axis representing a longitudinal direction of the insertion section 310, and is an angle representing a state whether or not the insertion section 310 is at a correct position with respect to the object. The imaging state may include information that identifies a wavelength band of a light source 352 used for imaging and information that identifies whether a pigment has been sprayed.

A change in the imaging state changes characteristics such as the position, size, and brightness of the region of interest on the image. Hence, it is not easy to create a classifier candidate that can be used for various kinds of imaging states for general purpose. Preparing the classifier candidates that are different in performance depending on the imaging state allows the user's preference to be more reflected on the detection result. Note that the difference in detection sensitivity to the imaging state may be attributed to the learning data, the model, or the pre-processing and the post-processing, similarly to the above-mentioned example. For example, with use of multitudes of images captured in a given imaging state for machine learning, it is possible to increase a detection sensitivity in the imaging state.

3. Display Example of Performance Information

Subsequently, a specific example of performance information displayed by the performance information processing section 120 is described. The performance information in accordance with the present embodiment may be, for example, comparison information indicating a difference in performance of the plurality of classifier candidates. With use of the comparison information, the user can easily recognize a difference in performance of two or more classification candidates from the display screen, and can thereby easily select a classifier candidate that is suited to his/her preference. The following description is also given of the example in which the performance information is the comparison information, but the performance information in accordance with the present embodiment is not prevented from being information indicating performance of a given classifier candidate alone. As the information indicating performance, various kinds of information, such as a detection result based on the input image, which will be described later, a detection result based on test data, and the learning data, can be used. The following description is given of an example of displaying performance information of two classifier candidates, but three or more classifier candidates may serve as a display target.

3.1 Display of Detection Result Based on Input Image

Figure 9:
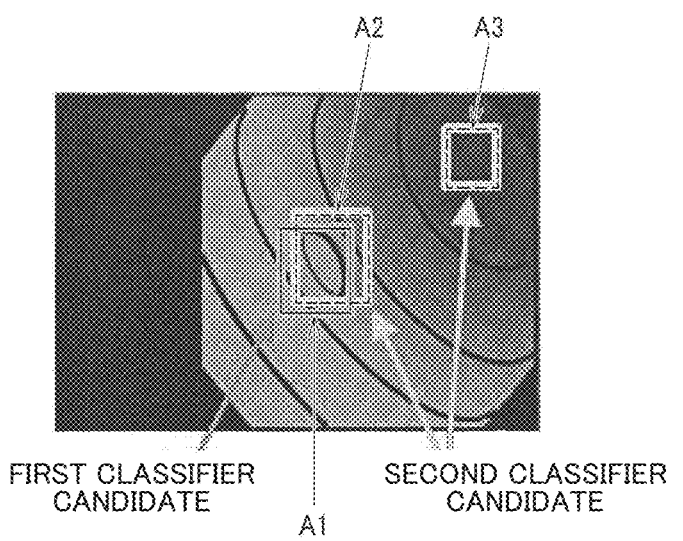
FIG. 9 illustrates an example of a screen displaying a detection result based on an input image.

FIG. 9 illustrates an example of a screen displaying the comparison information. As illustrated in FIG. 9, the performance information processing section 120 performs a process of displaying respective detection results from the plurality of classifier candidates as the performance information.

For example, the classification section 110 acquires an input image from the image acquisition section 331. The classification section 110 reads out the first classifier candidate from the storage section 333 and inputs the input image to the first classifier candidate to acquire a first detection result. The first detection result is, for example, information that identifies the position or size of the region of interest on the input image. The first detection result may be information that identifies a rectangular region including the region of interest in a limited sense. In addition, the classification section 110 reads out the second classifier candidate from the storage section 333 and inputs the input image to the second classifier candidate to acquire a second detection result. The second detection result is, for example, information that identifies a rectangular region including the region of interest.

The classification section 110 outputs the first detection result, the second detection result, and the input image to the performance information processing section 120. The performance information processing section 120 performs a process of causing the display section 340 to display an image in which the first detection result and the second detection result are superimposed on one input image. Note that the process of performing display by superimposing the detection results on the input image overlaps with processing performed by the display section 340 after selection of the classifier by the user. Thus, in a case where an image illustrated in FIG. 9 is displayed, the display processing section 336 may also serve as the performance information processing section 120.

In FIG. 9, the first detection result from the first classifier candidate corresponds to A1. The second detection result from the second classifier candidate corresponds to A2 and A3. A1 and A2 are information indicating the identical region of interest. That is, it is obvious from a screen in FIG. 9 that the second classifier candidate has detected two regions of interest, and the first classifier candidate has detected only one region of interest out of the two regions of interest. For example, a user who thinks that a degree of importance of the region of interest corresponding to A3 is high or thinks that there is a possibility that she/he may overlook the region of interest without display of the region of interest, it is assumed that he/she will select the second classifier candidate. In addition, a user who thinks that a degree of importance of the region of interest corresponding to A3 is low or thinks that there is a possibility that that she/he will not overlook the region of interest without display of the region of interest, it is assumed that he/she will select the first classifier candidate.

Figure 10:
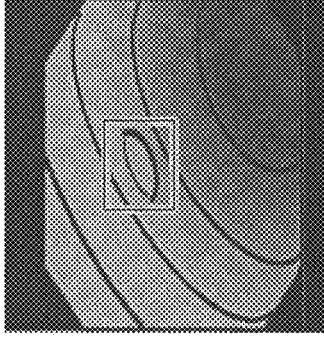
FIG. 10 illustrates an example of a screen displaying a detection result based on an input image.
Figure 10:
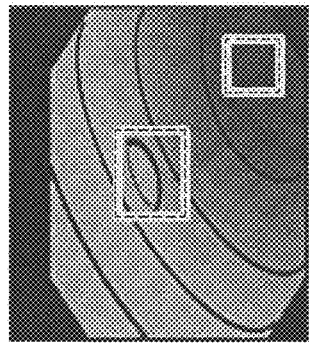

FIG. 10 illustrates another example of a screen displaying respective detection results as the comparison information. As illustrated in FIG. 10, the performance information processing section 120 may display a first image in which the first detection result from the first classifier candidate is superimposed on the input image and a second image in which the second detection result from the second classifier candidate is superimposed on the input image side by side. In other words, display screens illustrated in FIG. 10 corresponds to display screens obtained by dividing the display screen illustrated in FIG. 9 into two. Also in this case, it is obvious that the second classifier candidate has detected two regions of interest, and the first classifier candidate has detected only one region of interest out of the two regions of interest. This allows the user to grasp performance of each classifier candidate and select a classifier candidate that is suited to the user's preference.

As illustrated in FIGS. 9 and 10, the performance information processing section 120 performs a process of simultaneously displaying respective detection results with respect to the identical input image from the plurality of classifier candidates as the performance information. This enables simultaneous presentation of detection results from the plurality of classifier candidates using one screen, and thereby allows the user to easily make comparison and selection. However, the performance information processing section 120 may display the respective detection results from the plurality of classifier candidates at different timings. For example, the performance information processing section 120 may display the first image and the second image illustrated in FIG. 10 in a time-division manner.

In a case where the screen illustrated in FIG. 9 or FIG. 10 is displayed, a specific input image is required. Hence, for example, a processing procedure in this case is different from that illustrated in FIG. 3. First, the observation mode is started, the input image is acquired in the observation mode, and thereafter the performance information is displayed and the user's selection is received. Alternatively, an input image captured in an observation mode that has been previously performed is stored in the storage section 333, and the screen illustrated in FIG. 9 or FIG. 10 may be displayed using the input image. In this case, it is possible to display the performance information before the start of the observation mode as illustrated in FIG. 3.

3.2 Display of List of Detectable Lesions.

The performance information may be information that is acquired using test data. The test data is data that includes a plurality of test images, and in which information that identifies a lesion in each test image is known. The information that identifies the lesion is the presence/absence of the lesion, the position of the lesion, a result of classifying the lesion, and the like. That is, inputting the test image to the classifier candidate enables determination of whether or not the lesion included in the test image has been successfully and appropriately detected, or determination of whether or not a region that is not the lesion has been falsely detected as the lesion. Note that the test data may be evaluation data used at a learning stage, or may be data that is different from the evaluation data.

Figure 11:
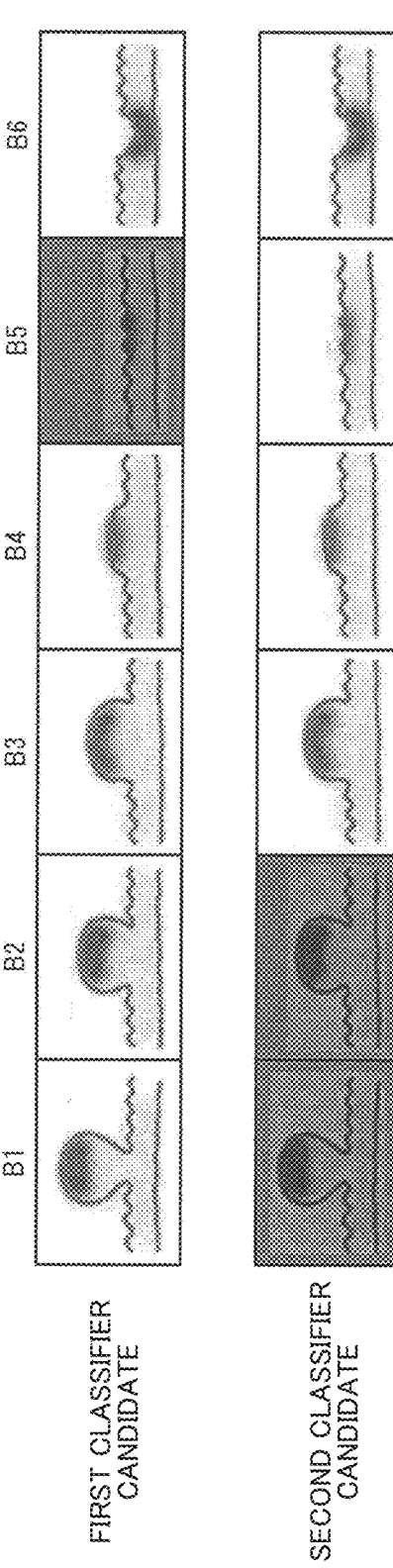
FIG. 11 illustrates an example of a screen displaying a list of detectable lesions.

FIG. 11 illustrates an example of a screen displaying performance information based on the test data. In this example, consideration is given to, for example, first to sixth lesions indicated in B1 to B6 as lesions included in the test data. Respective test images including the first to sixth lesions are input to each of the plurality of classifier candidates. Note that the process of inputting the test images to each classifier candidate and acquiring the detection result may be executed in the classification section 110, or may be executed in an external device outside the diagnosis support system 100.

For example, the first classifier candidate mentioned herein has successfully detected the first to fourth lesions and the sixth lesion, but has failed to detect the fifth lesion. In addition, the second classifier candidate has successfully detected the third to sixth lesions, but has failed to detect the first and second lesions.

The performance information processing section 120 performs a process of displaying a list of a plurality of regions of interest that is detectable by each of the plurality of classifier candidates. In the above-mentioned example, five lesions of the first to fourth lesions and the sixth lesion are displayed as a list with respect to the first classifier candidate. Similarly, four lesions of the third to sixth lesions are displayed as a list with respect to the second classifier candidate. In the example illustrated in FIG. 11, the lesions that have been successfully detected by each classifier candidate are displayed in a relatively bright manner. This enables presentation of to what type of lesion detection each classifier candidate is suited using specific lesions, and can thereby facilitate the user's selection.

For example, the region of interest corresponds to the lesion, and the performance information processing section 120 may perform a process of displaying a list of a plurality of lesions that is detectable by each of the plurality of classifier candidates, regarding each of a protruding lesion, a flat lesion, and a depressed lesion. In the example illustrated in FIG. 11, the first to third lesions indicated in B1 to B3, respectively, each correspond to the protruding lesion, the fourth and fifth lesions indicated in B4 and B5, respectively, each correspond to the flat lesion, and the sixth lesion indicated in B6 corresponds to the depressed lesion. This enables display of a list indicating differences in performance in accordance with a shape and type of the lesion, and can thereby facilitate the user's selection. In the example in FIG. 11, it is found that the first classifier candidate is suited to detection of the protruding lesion, and the first classifier candidate is suited to detection of the flat lesion and the depressed lesion.

As illustrated in FIG. 11, the performance information processing section 120 may display a list indicating whether or not each classifier candidate has successfully detected each of a plurality of lesions included in the test images. For example, the display also includes display of the first classifier candidate having failed to detect the fifth lesion and the second classifier candidate having failed to detect the first and second lesions. In the example illustrated in FIG. 11, the lesions that have failed to be detected by each classifier candidate are displayed in a relatively dark manner. This enables presentation of to what kind of lesion detection each classifier candidate is not suited using specific lesions, and can thereby facilitate the user's selection. For example, with respect to the protruding lesion, the display clearly indicates that the first classifier candidate has successfully detected a plurality of protruding lesions, while the second classifier candidate has failed to detect some of the plurality of protruding lesions, and can thereby facilitate the user's selection.

3.3 Display of Data Indicating Classification Performance

The description has been given of the example of displaying the list of the information regarding whether or not specific lesions have been successfully detected by each classifier candidate, with reference to FIG. 11. However, the method for displaying the performance information based on the test data is not limited thereto.

Figures 12A, 12B, 12C:
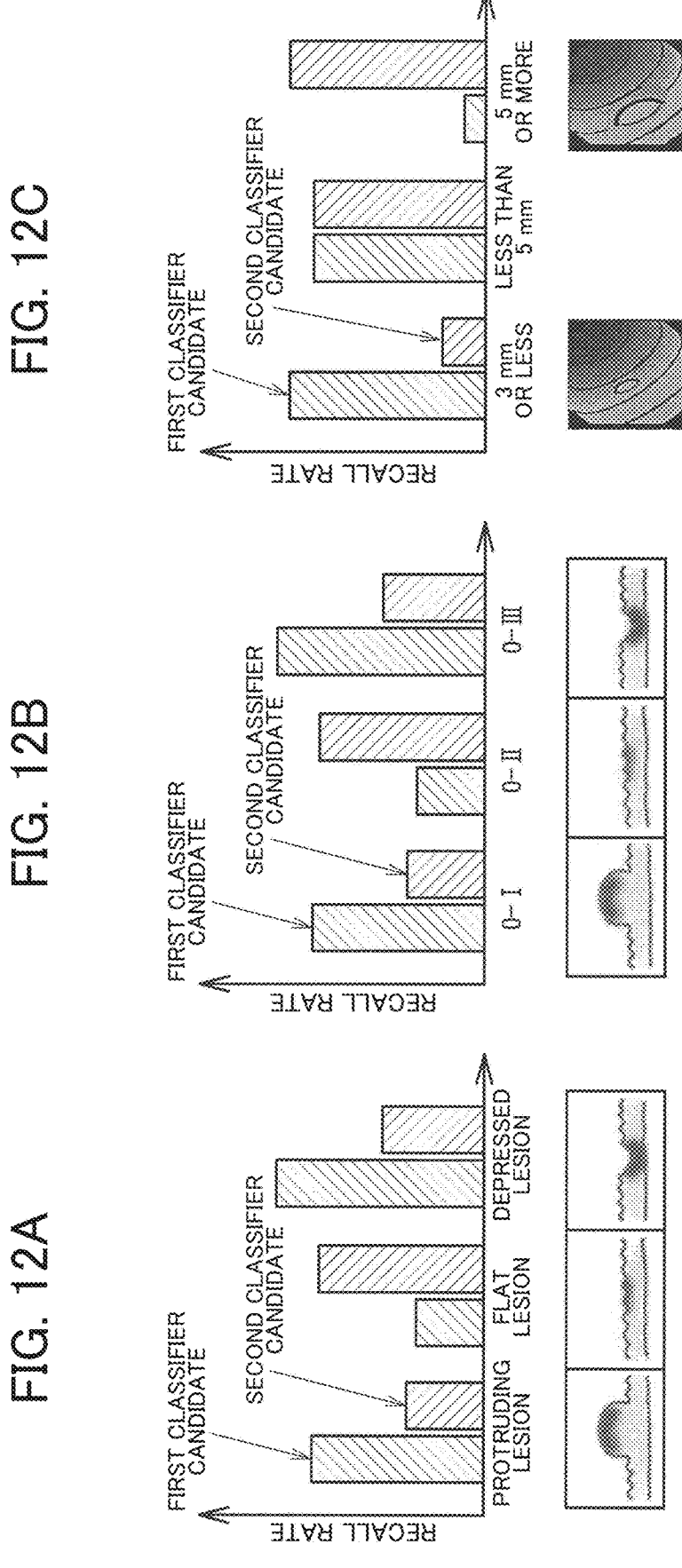
FIGS. 12A to 12C each illustrate an example of a screen displaying a list of classification performance such as a recall rate.

FIG. 12A illustrates an example of a screen displaying data indicating classification performance as the performance information. As described above, classification results such as the shape, degree of malignancy, and size of the lesion included in the test image may be associated with the test image. For example, assume that data including x1 protruding lesions, x2 flat lesions, and x3 depressed lesions has been acquired as test data. By inputting the test data to the first classifier candidate, obtained is a detection result indicating that y1 protruding lesions, y2 flat lesions, and y3 depressed lesions have been appropriately detected. By inputting the identical test data to the second classifier candidate, obtained is a detection result indicating that z1 protruding lesions, z2 flat lesions, and z3 depressed lesions have been appropriately detected.

The performance information processing section 120, for example, acquires a recall rate as data indicating the classification performance. The recall rate represents, assuming that the number of cases in which the lesion has been successfully and correctly detected as the lesion is A and the number of cases in which the lesion has been falsely detected as being not the lesion is B, a ratio of A to A+B. The recall rate is an index that enables identification of a ratio of overlooking. In the above-mentioned example, a recall rate of the first classifier candidate with respect to the protruding lesion corresponds to y1/x1, a recall rate of the first classifier candidate with respect to the flat lesion is y2/x2, and a recall rate of the first classifier candidate with respect to the depressed lesion corresponds to y3/x3. A recall rate of the second classifier candidate with respect to the protruding lesion corresponds to z1/x1, a recall rate of the second classifier candidate with respect to the flat lesion is z2/x2, and a recall rate of the second classifier candidate with respect to the depressed lesion corresponds to z3/x3.

In the example in FIG. 12A, the recall rate of the first classifier candidate and the recall rate of the second classifier candidate are displayed for each lesion type. This enables display of whether each classifier candidate is suited to detection of the protruding lesion, the flat lesion, and the depressed lesion using a statistical index value in an easily understood manner.

The performance information processing section 120 may display the recall rate of each classifier candidate with respect to each medical classification of the lesion, as illustrated in FIG. 12B. Alternatively, the performance information processing section 120 may display the recall rate of each classifier candidate with respect to each size of the lesion, as illustrated in FIG. 12C. This enables display of to what kind of lesion detection each classifier candidate is suited in an easily understood manner. The performance information processing section 120 may display the recall rate in accordance with another condition such as a color of the lesion.

Figures 13, 14:
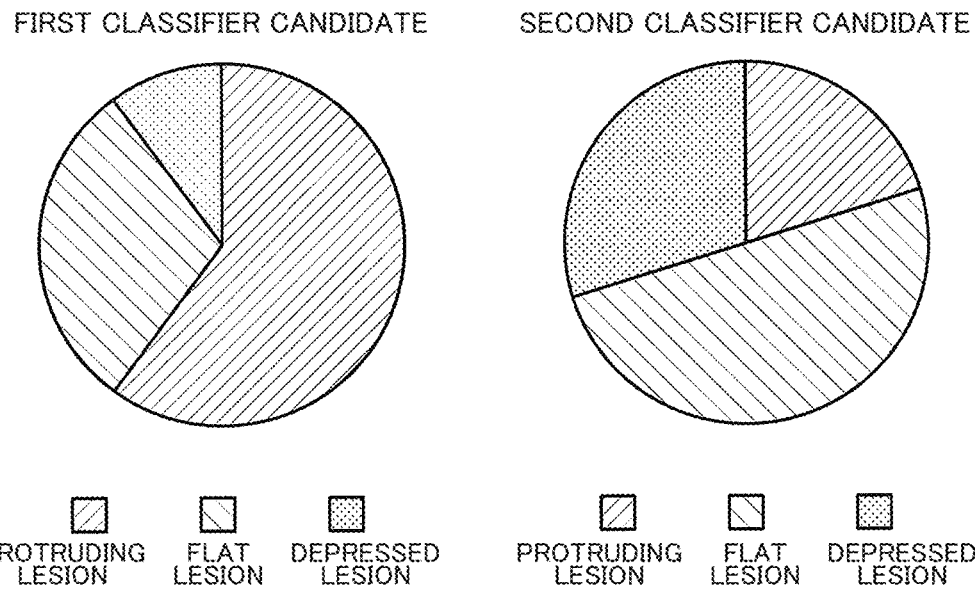
FIG. 13 illustrates an example of a screen displaying classification performance such as a recall rate.
FIG. 14 illustrates an example of a screen displaying learning data.

Display of data indicating the classification performance is not limited to display using a graph. FIG. 13 illustrates another example of a screen displaying data indicating the classification performance. As illustrated in FIG. 13, the performance information processing section 120 may use a table to display the recall rate of each classifier candidate with respect to each type of the lesion. Also in this case, it is possible to display to what kind of lesion detection each classifier candidate is suited using a statistical index value in an easily understood manner.

The above description has been given of the example using the recall rate as the data indicating the classification performance. However, the performance information processing section 120 may display another index such as specificity and a rate of correct answers. The specificity represents, assuming that the number of cases in which a region that is not the lesion has been correctly detected as being not the lesion is C and the number of cases in which the region that is not the lesion has been falsely detected as the lesion is D, a ratio of C to C+D. The specificity can be used as an index for determining whether or not the region that is not the lesion is suspected indiscriminately.

The rate of correct answers represents a ratio of A+C to a total number of cases. As described above, A is the number of cases in which the lesion has been successfully and correctly detected as the lesion, and C is the number of cases in which the region that is not the lesion has been correctly detected as being not the lesion. The total number of cases corresponds to A+B+C+D. The rate of correct answers represents a ratio of determination that has been made correctly, and thus serves as a simple and easy-to-understand index.

As described above, the performance information processing section 120 may perform a process of displaying the classification performance of the plurality of classifier candidates as the performance information. The data indicating the classification performance is, for example, a statistical index, and may be the recall rate, the specificity, or the rate of correct answers as described above. This enables presentation of the classification performance of the classifier candidate using the easy-to-understand index to the user.

At this time, the performance information processing section 120 may perform a process of displaying data indicating respective detection results from the plurality of classifier candidates with respect to the test data as the data indicating the classification performance of the plurality of classifier candidates. The test data is data for determining the classification performance, and the information regarding the presence/absence of the region of interest, the position of the region of interest, the size of the region of interest, and the classification result of the region of interest has been known, as described above. With use of the test data, it is possible to appropriately determine the classification performance of the classifier candidate.

3.4 Display Based on Previous Examination Result

The input image is an in-vivo image in which the living body is captured, and the performance information processing section 120 may display data indicating appropriateness of a detection result in previous examination using an in-vivo image as the data indicating the classification performance of the plurality of classifier candidates.

For example, after a given classifier candidate is selected by the user's selection as the classifier, the detection result using the classifier is displayed. In a case where the user performs some kind of action on the display, the action is fed back, whereby the data indicating the classification performance is generated.

The feedback made by the user is, for example, an input regarding resection of the living body and a result of pathologic analysis on the resected living body. For example, the user resects and removes a region presented by the classifier as the lesion using a treatment tool such as an energy device. The pathologic analysis is performed on the resected portion of the living body. The user feeds back information indicating whether or not the resected portion of the living body is the lesion as presented by the classifier based on the result of the pathologic analysis. For example, the performance information processing section 120 obtains a ratio of the number of resected portions of living bodies being the lesion as indicated by the detection result with respect to a total number of resections, and can thereby obtain an index similar to the above-mentioned rate of correct answers.

Alternatively, the feedback from the user may be information indicating a relationship between a region that is designated by the user as a target of treatment such as resection and a lesional region presented by the classifier. More specifically, when performing a treatment on a region that has not been presented as the lesion by the classifier, the user feeds back information indicating to this effect. This corresponds to the fact that the lesion that had failed to be detected by the classifier has been uniquely detected and treated by the user. Thus, the performance information processing section 120 is capable of obtaining, based on the feedback from the user, an index representing a ratio of determination that has been falsely made as the lesion being not the lesion.

Note that the data indicating appropriateness of the detection result in the previous examination can be obtained as numeric value data similarly to the example using the test data. Hence, the performance information processing section 120 may perform a process of using a graph as illustrated in each of FIGS. 12A to 12C or a process of using a table as illustrated in FIG. 13 to display the data indicating appropriateness of the detection result in the previous examination.

3.5 Display of Learning Data

The above description has been given of the example in which the performance information is a detection result itself obtained by inputting of some kind of image to the classifier candidate, or information obtained based on the detection result. However, the performance information in accordance with the present embodiment is not limited to information that requires acquisition of the detection result.

FIG. 14 illustrates another example of a screen displaying the performance information. As illustrated in FIG. 14, the performance information processing section 120 may perform a process of displaying learning data used for learning of the plurality of classifier candidates as data indicating the classification performance of the plurality of classifier candidates. In FIG. 14, a ratio of each of the protruding lesion, the flat lesion, and the depressed lesion included in the learning data with respect to each of the first classifier candidate and the second classifier candidate is displayed with a circle graph. In the example illustrated in FIG. 14, it can be found that the learning data of the first classifier candidate has a higher ratio of the protruding lesion, and the learning data of the second classifier candidate has a higher ratio of the flat lesion. Thus, the user can presume that the first classifier candidate is suited to detection of the protruding lesion, and the second classifier candidate is suited to detection of the flat lesion.

As described above, the display mode for the performance information in accordance with the present embodiment can be modified in various manners. For example, using the specific detection results as illustrated in FIGS. 9 to 13 is advantageous in that accuracy of the performance information of the classifier candidate can be increased. In contrast, using the learning data as illustrated in FIG. 14 is advantageous in easiness of generation and display of the performance information because a specific detection result is unnecessary.

4. Modification

Some modifications will be described below.

The user's selection receiving section 130 may be capable of receiving the user's selection for selecting two or more classifier candidates among the plurality of classifier candidates. The classification section 110 performs a process of selecting the classifier from the two or more classifier candidates selected by the user. This allows the diagnosis support system 100 to support selection of the classifier in a case where the user cannot narrow down to one classifier candidate by merely seeing the performance information.

The classification section 110 may select the classifier based on a degree of reliability representing a degree of probability of the detection result. For example, in a case where a learning model classifies two regions including a lesional region and a normal region, the output layer of the trained model outputs a degree of probability that a target region is the lesional region and a degree of probability that the target region is the normal region. In a case where the output layer is a publicly-known softmax layer, the degree of probability that the target region is the lesional region and the degree of probability that the target region is the normal region are such probability data as that a sum of them becomes 1. For example, in a case where the probability that the target region is the lesional region is a given threshold or more, the classification section 110 determines that the lesion has been detected, and outputs the detection result.

Assume that the first classifier candidate and the second classifier candidate are selected from three or more classifier candidates based on the user's selection. The classification section 110, for example, performs a process of inputting the input image to each of the first classifier candidate and the second classifier candidate in the observation mode. The classification section 110 compares a degree of reliability representing the degree of probability of the lesional region output from the first classifier candidate and a degree of reliability output from the second classifier candidate with each other, and performs a process of automatically selecting a classifier candidate having a larger value as the classifier. This enables automatic selection of the classifier candidate having a higher degree of reliability.

The user's selection receiving section 130 may receive selection of classifiers made by a plurality of users. For example, the diagnosis support system 100 in accordance with the present embodiment is installed in each hospital, and a plurality of classifier candidates is different for each hospital. The plurality of classifier candidates being different means that not all the classifier candidates are matched with each other, and part of the classifier candidates may overlap with each other as the above-mentioned original classifier. Since classifier candidates in a given hospital include, for example, the customized classifier candidate, the diagnosis support system 100 is considered to have characteristics that are suited to the hospital. However, it is assumed that a plurality of users having different preferences utilizes the diagnosis support system 100 even within one hospital. In this respect, allowing the plurality of users to individually select classifiers enables switching of a detection result that is suited to the user's selection even within a group using one diagnosis support system 100. Specifically, the classification section 110 outputs the detection result from the classifier in accordance with the user.

At this time, the storage section (for example, the storage section 333) may store a selection history of classifiers for each user. This enables change of a default classifier for each user, and can thereby reduce a burden on a user regarding selection of a classifier for the second and subsequent times.

Before observation of the input image by the user, the user's selection receiving section 130 may receive, after receiving the user's first selection of the classifier, the user's second selection during the user's observation of the input image.

Figure 15:
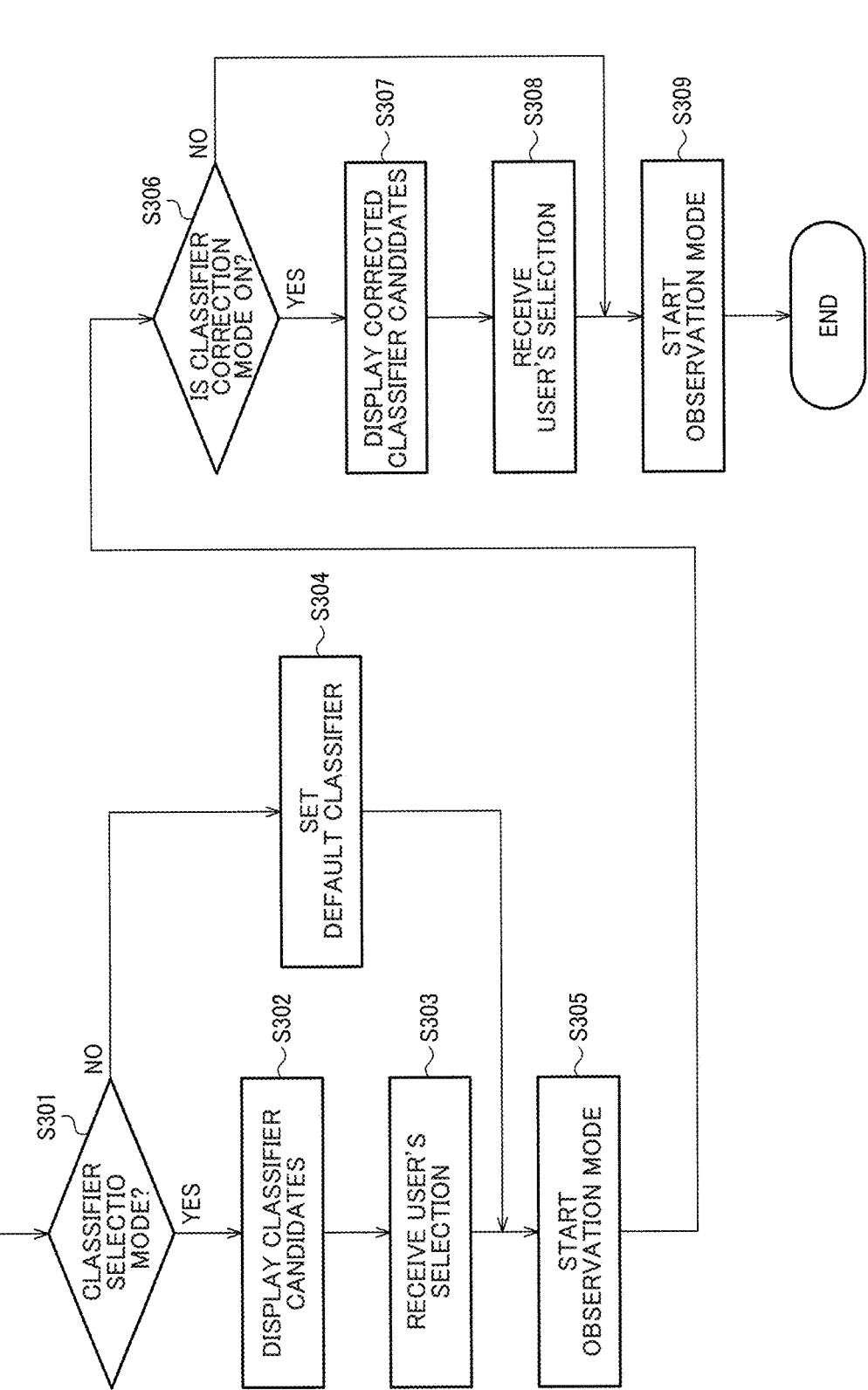
FIG. 15 is another flowchart describing processing in the diagnosis support system.

FIG. 15 is a flowchart for describing processing of the present modification. Steps S301 to S305 in FIG. 15 are similar to steps S101 to S105 in FIG. 3, respectively. That is, the diagnosis support system 100 can receive the first selection, which is the user's selection for selecting the classifier, before the start of the observation mode.

After the start of the observation mode in step S305, in step S306, the control section 332 of the endoscope system 300 determines whether or not an operation mode of the diagnosis support system 100 is a classifier correction mode.

In a case of YES in step S306, in step S307, the performance information processing section 120 performs a process of displaying the performance information of classifier candidates. In step S308, the user's selection receiving section 130 performs a process of receiving the user's selection for selecting any of the classifier candidates. The classification section 110 identifies the classifier candidate selected by the user as the classifier used for outputting of the detection result.

In a case of NO in step S306, the user's selection receiving section 130 does not receive the second selection, which is the user's selection for correcting the classifier. In this case, for example, the classification section 110 identifies the classifier candidate selected in the first selection or the default classifier candidate as the classifier used for outputting of the detection result.

After the processing in step S308 or in a case of NO in step S306, in step S309, the diagnosis support system 100 resumes the operation in the observation mode.

This enables reception of the user's selection multiple times at the time of single observation for detecting the lesion. Receiving the first selection first before the observation enables smooth start of display of the detection result when the lesion appears in the image. In addition, receiving the second selection during the observation enables, in a case where an actual detection result is not matched with the user's preference, switching of the detection result in accordance with the preference. Note that performance information displayed for the first selection and performance information displayed for the second selection may be identical information, or may be different information. Note that correction of the classifier may be executed twice or more during the single observation.

The plurality of classifier candidates in accordance with the present embodiment may include two or more classifier candidates generated by making different settings to a common trained model. A setting made to the trained model is, specifically, a threshold used at the time of determination that the region of interest has been detected. For example, as described above, the trained model outputs the degree of probability that the target is the region of interest. In a case where the degree of probability is the threshold or more, the trained model determines that the region of interest has been detected. Changing the threshold can change a detection sensitivity to the region of interest. That is, changing the setting of the trained model can facilitate generation of the plurality of classifier candidates having different detection sensitivities. At this time, since the performance information is displayed in the method in accordance with the present embodiment, it is possible to present a difference in detection result with a change in threshold to the user in an easily understood manner.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. A diagnosis support system comprising a processor, the processor being connected to a plurality of classifier candidates that are different in performance; the processor being configured to:
   apply the plurality of classifier candidates to a first input image to obtain performance information corresponding to each of the plurality of classifier candidates, the first input image being an in-vivo image, wherein the performance information includes comparison information indicating differences in performance among the plurality of classifier candidates based on detection of a region of interest in the in-vivo image;
   display the performance information of each of the plurality of classifier candidates side by side;
   receive a user's selection of the performance information displayed side by side; and
   based on the user's selection, input a second input image to a corresponding one of the plurality of classifier candidates, the corresponding one of the plurality of classifier candidates being associated with the performance information selected by the user.

2. The diagnosis support system as defined in claim 1, wherein
   the first input image is used for acquiring the performance information and is one of a real-time image, a test image, or an image from a previous examination, and
   the second input image input after the user's selection is a real-time image.

3. The diagnosis support system as defined in claim 1, wherein the plurality of classifier candidates has mutually different detection sensitivities to absence or presence of a region of interest.

4. The diagnosis support system as defined in claim 3, wherein the plurality of classifier candidates has at least one of the mutually different detection sensitivities to a shape of the region of interest, the mutually different detection sensitivities to a size of the region of interest, or the mutually different detection sensitivities to a color of the region of interest.

5. The diagnosis support system as defined in claim 3, wherein
   the region of interest is a region corresponding to a lesion, and
   the plurality of classifier candidates has mutually different detection sensitivities to medical classification of the region of interest.

6. The diagnosis support system as defined in claim 1, wherein the plurality of classifier candidates output mutually different detection results depending on an imaging state when the first input image is captured.

7. The diagnosis support system as defined in claim 1, wherein the plurality of classifier candidates use mutually different processing methods with respect to the first input image.

8. The diagnosis support system as defined in claim 1, wherein the plurality of classifier candidates include an original classifier candidate and a customized classifier candidate created by the user.

9. The diagnosis support system as defined in claim 8, wherein the customized classifier candidate is created based on machine learning using learning images including an image held by the user.

10. The diagnosis support system as defined in claim 1, wherein the processor is configured to perform a process of displaying respective detection results of the plurality of classifier candidates as the performance information.

11. The diagnosis support system as defined in claim 10, wherein the processor is configured to perform a process of simultaneously displaying respective detection results of the plurality of classifier candidates with respect to an identical first input image as the performance information.

12. The diagnosis support system as defined in claim 1, wherein the processor is configured to perform a process of displaying a list of a plurality of regions of interest that is detectable by each of the plurality of classifier candidates.

13. The diagnosis support system as defined in claim 12, wherein each region of interest is a region corresponding to a lesion, and the processor is configured to perform a process of displaying a list of a plurality of the lesions that is detectable by each of the plurality of classifier candidates, regarding each of a protruding lesion, a flat lesion, and a depressed lesion.

14. The diagnosis support system as defined in claim 1, wherein the processor is configured to perform a process of displaying data indicating a classification performance of the plurality of classifier candidates as the performance information.

15. The diagnosis support system as defined in claim 14, wherein the processor is configured to perform a process of displaying data indicating respective detection results of the plurality of classifier candidates with respect to test data as data indicating the classification performance of the plurality of classifier candidates.

16. The diagnosis support system as defined in claim 14, wherein the processor is configured to perform a process of displaying learning data used for learning of the plurality of classifier candidates as the data indicating the classification performance of the plurality of classifier candidates.

17. The diagnosis support system as defined in claim 14, wherein the first input image is an in-vivo image in which a living body is captured, and the processor is configured to perform a process of displaying data indicating appropriateness of a detection result in previous examination using the in-vivo image as the data indicating the classification performance of the plurality of classifier candidates.

18. The diagnosis support system as defined in claim 1, wherein the processor is configured to receive the user's selection for selecting two or more classifier candidates among the plurality of classifier candidates, and the processor is configured to perform a process of selecting a classifier candidate among the two or more classifier candidates selected by the user.

19. The diagnosis support system as defined in claim 1, wherein the processor is configured to receive a selection of respective classifier candidates by a plurality of the users, and output a detection result from each of the classifier candidates in accordance with the user.

20. The diagnosis support system as defined in claim 1, wherein the processor is configured to:

receive the user's first selection of a corresponding one of the classifier candidates before the user's observation of the second input image, and thereafter receive the user's second selection of a corresponding one of the classifier candidates during the user's observation of the second input image.

21. The diagnosis support system as defined in claim 1, wherein the plurality of classifier candidates includes two or more of the classifier candidates generated by making different settings to a common trained model.

22. The diagnosis support system as defined in claim 1, wherein the processor is configured to display at least two types of performance that are in a trade-off relationship as the performance information.

23. The diagnosis support system as defined in claim 22, wherein the performance in the trade-off relationship is detection accuracy and processing time, or detection accuracy and a frequency of displaying a detection result.

24. A diagnosis support method comprising:

applying a plurality of classifier candidates to a first input image to obtain performance information corresponding to each of the plurality of classifier candidates, the first input image being an in-vivo image, wherein the performance information includes comparison information indicating differences in performance among the plurality of classifier candidates based on detection of a region of interest in the in-vivo image, the plurality of classifier candidates outputting mutually different detection results when detecting the region of interest from the first input image;

displaying the performance information of each of the plurality of classifier candidates side by side;

receiving a user's selection for selecting at least one of the plurality of classifier candidates as a classifier serving as an output target;

based on the user's selection, input a second input image to a corresponding one of the plurality of classifier candidates, the corresponding one of the plurality of classifier candidates being associated with the performance information selected by the user; and outputting a detection result of the classifier selected by the user's selection, the displaying including presenting at least two types of performance that are in a tradeoff relationship as the performance information.

25. A non-transitory computer-readable storage medium storing a diagnosis support program that causes a computer to implement:

applying a plurality of classifier candidates to a first input image to obtain performance information corresponding to each of the plurality of classifier candidates, the first input image being an in-vivo image, wherein the performance information includes comparison information indicating differences in performance among the plurality of classifier candidates based on detection of a region of interest in the in-vivo image, the plurality of classifier candidates outputting mutually different detection results when detecting the region of interest from the first input image;

displaying the performance information of each of the plurality of classifier candidates side by side;

receiving a user's selection for selecting at least one of the plurality of classifier candidates as a classifier serving as an output target;

based on the user's selection, input a second input image to a corresponding one of the plurality of classifier candidates, the corresponding one of the plurality of classifier candidates being associated with the performance information selected by the user; and outputting a detection result of the classifier candidate selected by the user's selection.

\* \* \* \* \*